(12) United States Patent
Medof et al.

(10) Patent No.: US 8,940,299 B2
(45) Date of Patent: Jan. 27, 2015

(54) METHOD OF TREATING CANCER

(75) Inventors: M. Edward Medof, Pepperpike, OH (US); Michael G. Strainic, Westlake, OH (US); Young A Choi, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 142 days.

(21) Appl. No.: 12/920,293

(22) PCT Filed: Mar. 2, 2009

(86) PCT No.: PCT/US2009/035722
§ 371 (c)(1),
(2), (4) Date: Nov. 23, 2010

(87) PCT Pub. No.: WO2009/108931
PCT Pub. Date: Sep. 3, 2009

(65) Prior Publication Data
US 2011/0135656 A1 Jun. 9, 2011

Related U.S. Application Data

(60) Provisional application No. 61/032,330, filed on Feb. 28, 2008.

(51) Int. Cl.
| | | |
|---|---|---|
| *A61K 39/395* | (2006.01) | |
| *A61K 39/00* | (2006.01) | |
| *C12N 15/11* | (2006.01) | |
| *A61K 38/00* | (2006.01) | |
| *C07K 16/28* | (2006.01) | |
| *C12N 15/113* | (2010.01) | |
| *A61K 38/08* | (2006.01) | |
| *A61K 38/10* | (2006.01) | |

(52) U.S. Cl.
CPC .......... *C07K 16/2896* (2013.01); *C07K 2316/96* (2013.01); *C12N 2310/14* (2013.01); *A61K 39/395* (2013.01); *A61K 38/00* (2013.01); *A61K 38/08* (2013.01); *C12N 15/1138* (2013.01); *A61K 38/10* (2013.01); *A61K 2039/505* (2013.01); *A61K 39/00* (2013.01)
USPC ............ 424/130.1; 424/133.1; 424/135.1; 424/158.1; 424/174.1; 514/44 A; 530/300

(58) Field of Classification Search
None
See application file for complete search history.

(56) References Cited

U.S. PATENT DOCUMENTS

| | | | |
|---|---|---|---|
| 2004/0228860 A1 | 11/2004 | Taylor et al. | |
| 2005/0147605 A1* | 7/2005 | Rosen ...................... | 424/143.1 |
| 2006/0140936 A1* | 6/2006 | Goldenberg et al. ...... | 424/133.1 |
| 2007/0178068 A1 | 8/2007 | Reich et al. | |
| 2011/0044983 A1 | 2/2011 | Lambris et al. | |

FOREIGN PATENT DOCUMENTS

WO  WO 2007051063 A2 *  5/2007

OTHER PUBLICATIONS

Carina Dennis, "Off by a whisker" Nature, 442(17), 2006, pp. 739-741.*
Fortney et al. "Integrative computational biology for cancer research" Hum Genet, 2011, 130, pp. 465-481.*
Markiewski, Maciej M., "Unwelcome Complement", Cancer Res. 2009; 69: (16). Aug. 15, 2009.
Markiewski, Maciej M., "Is Complement good or bad for cancer patients? A new perspective on an old dilemma", Trends in Immunology vol. 30 No. 6.
Monk, PN, et al. "Function, Structure and therapeutic potential of complement C5a receptors", British Journal of Pharmacology (2007) 152, 429-448.

* cited by examiner

*Primary Examiner* — Daniel E Kolker
*Assistant Examiner* — James Rogers
(74) *Attorney, Agent, or Firm* — Tarolli, Sundheim, Covell & Tummino LLP

(57) ABSTRACT

A method for inducing apoptosis of a neoplastic cell expressing C3aR or C5aR includes administering at least one complement antagonist to the cell so that the at least one complement antagonist substantially reduces or inhibits the activity of protein kinase B in the neoplastic cell.

18 Claims, 28 Drawing Sheets

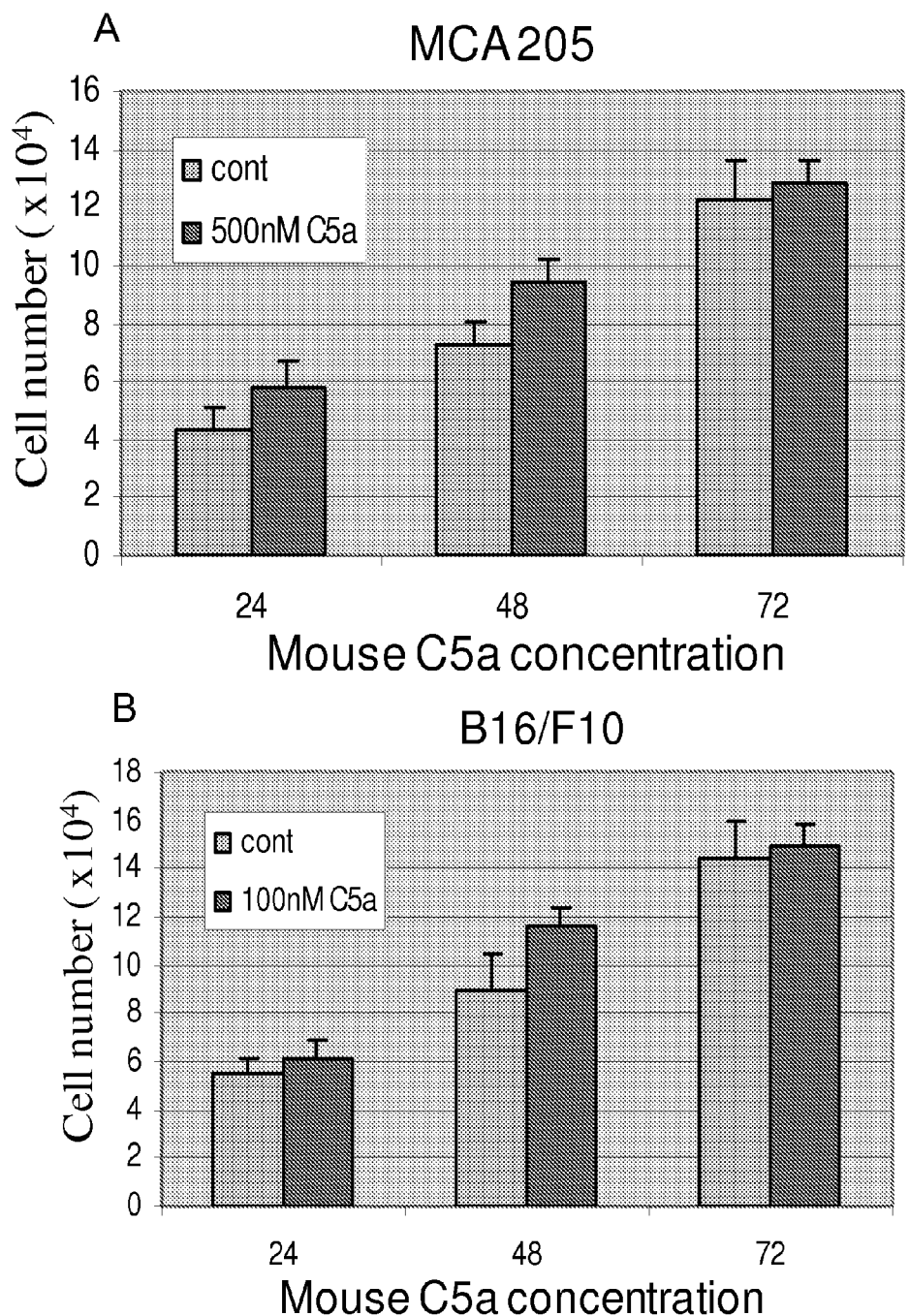
Fig. 2A-B

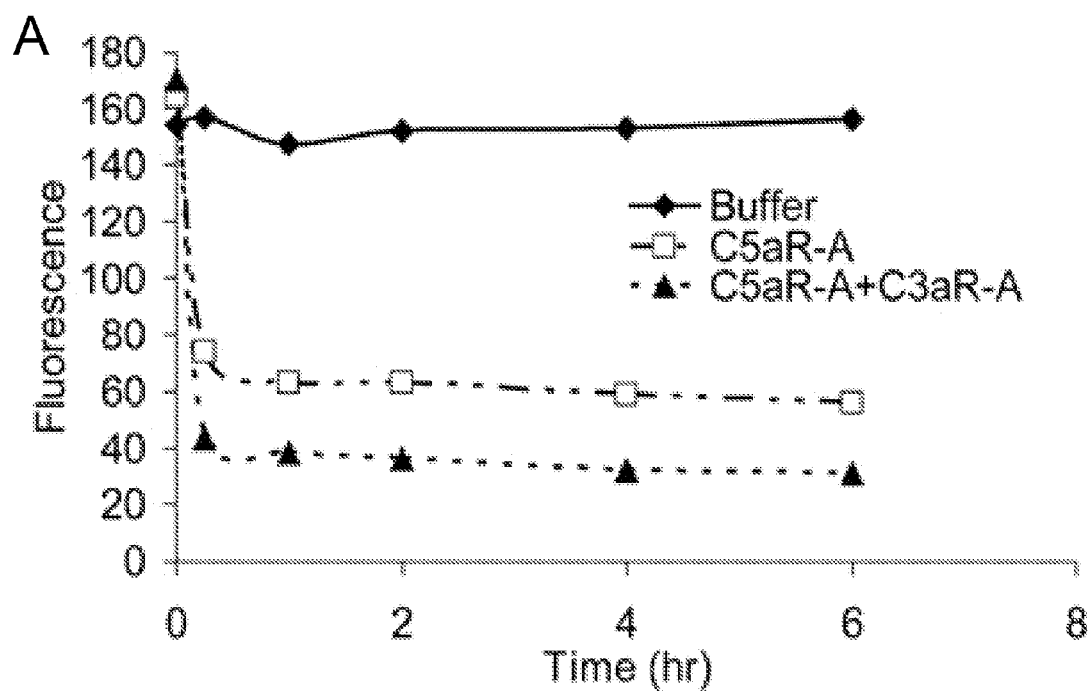
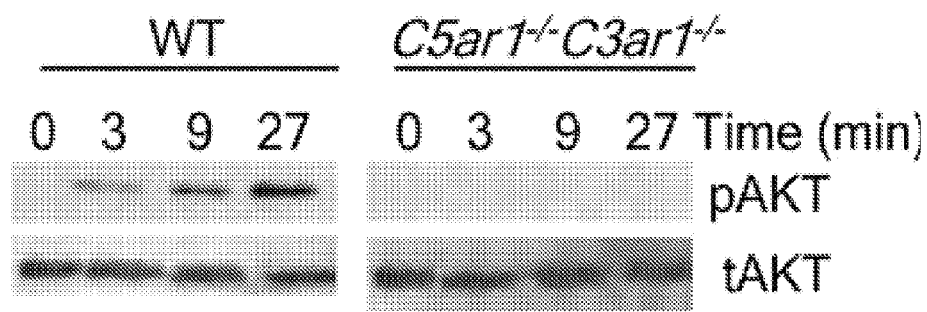
Fig. 5A

A
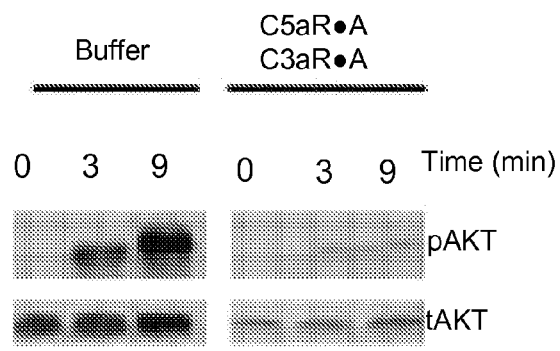
B
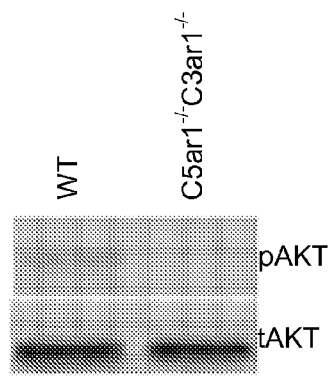
Figs. 6A-B

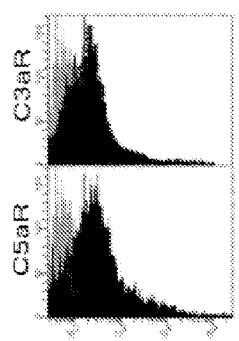
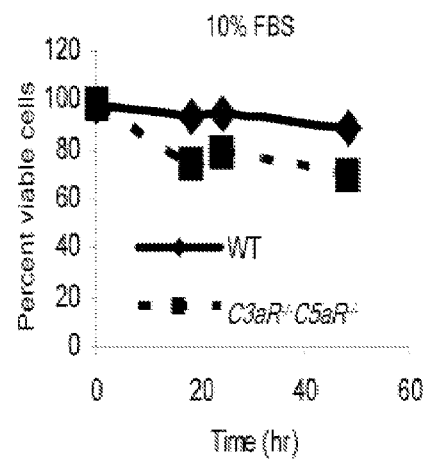
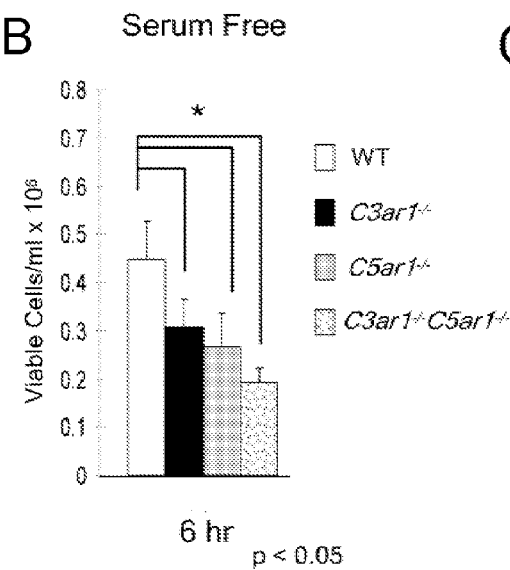
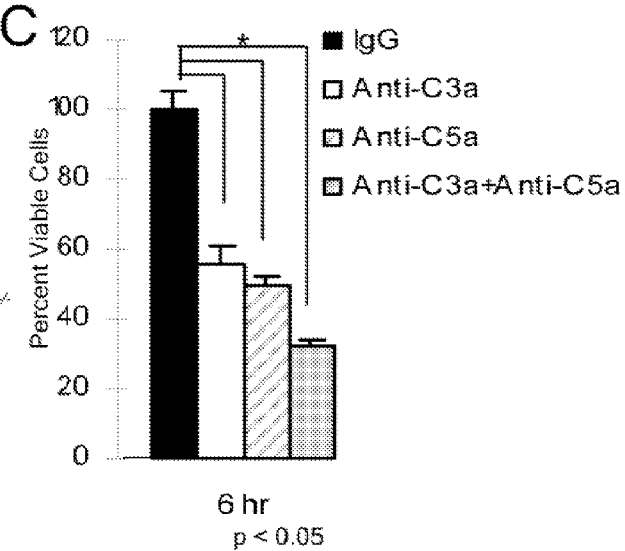
Figs. 7A-C

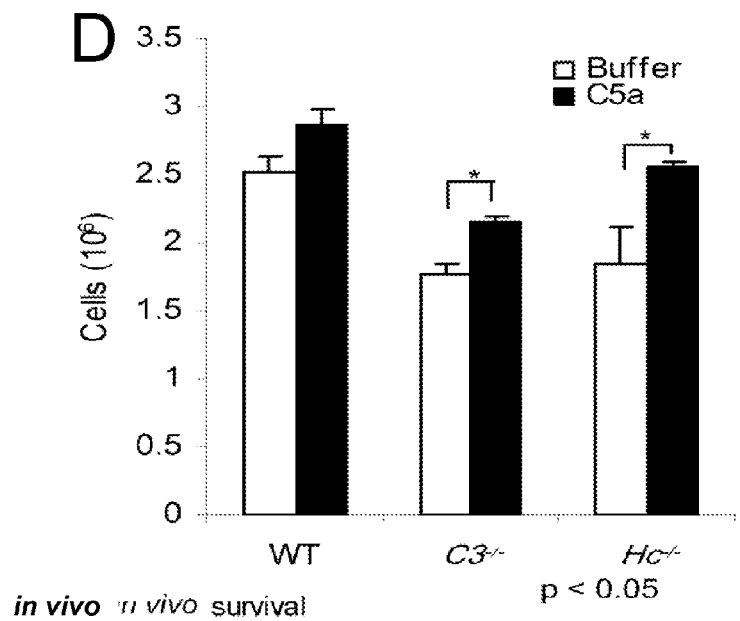
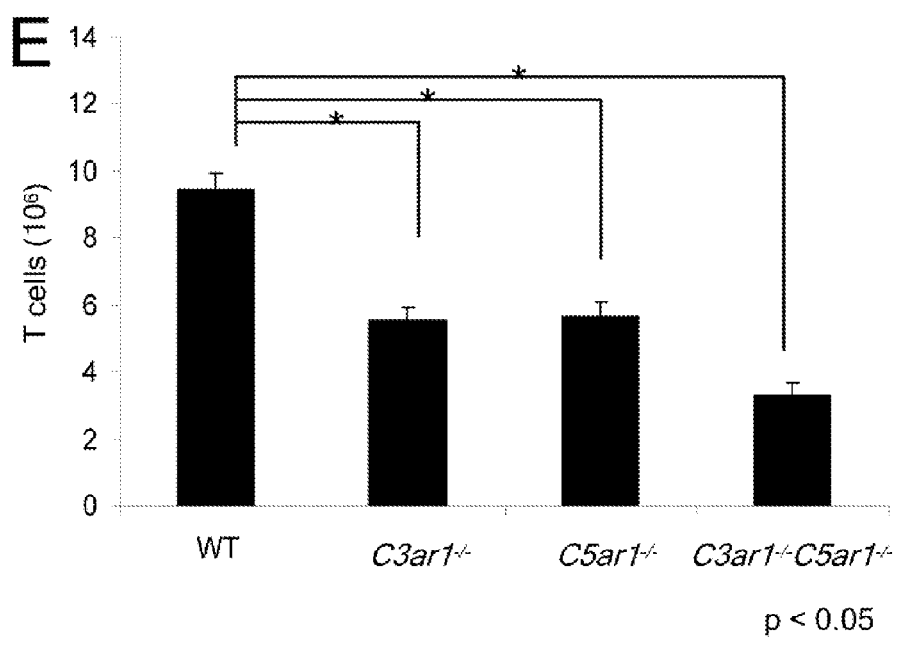
Figs. 7D-E

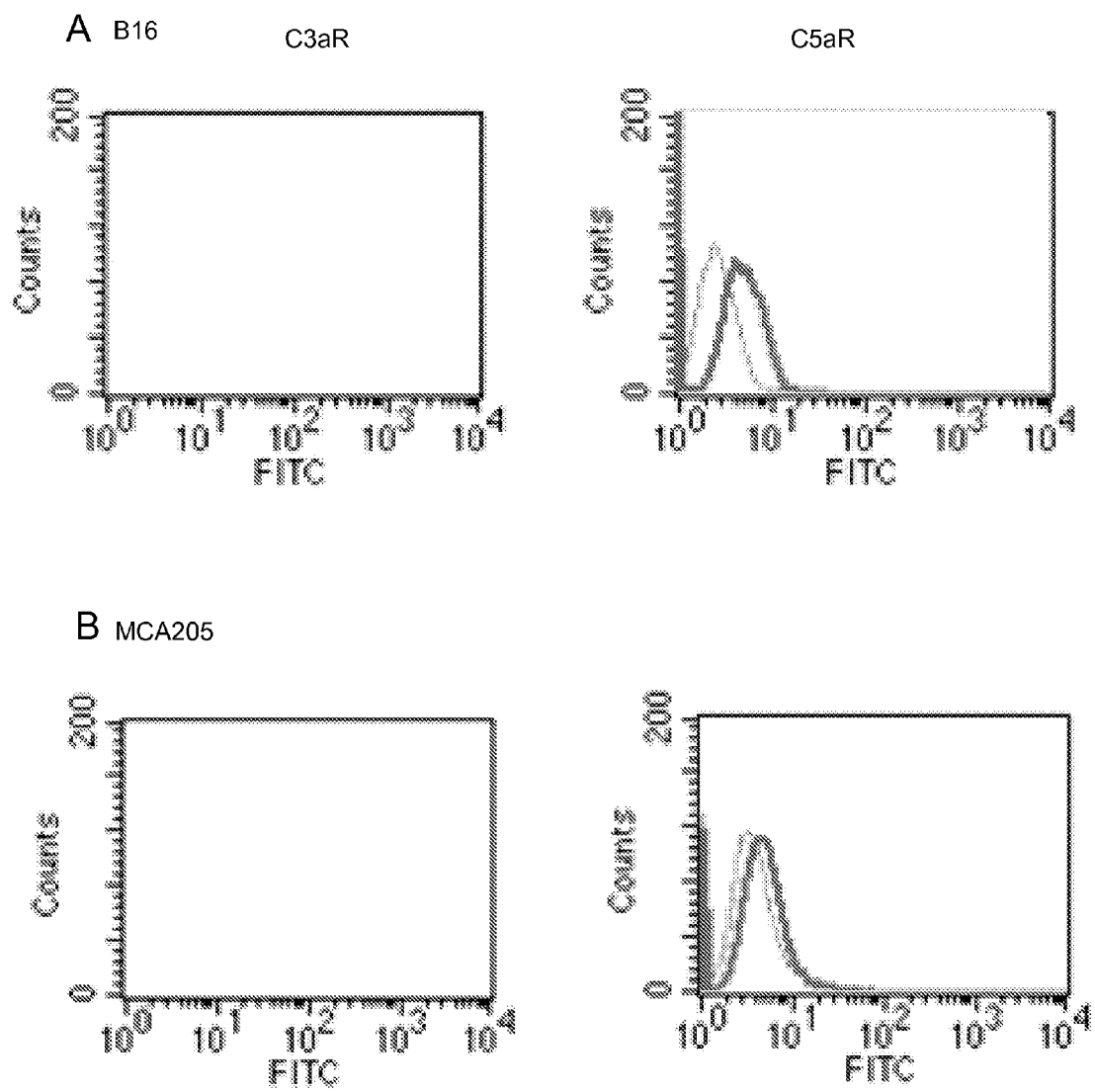
Fig. 8A-B (a) B16

(b) MCA205

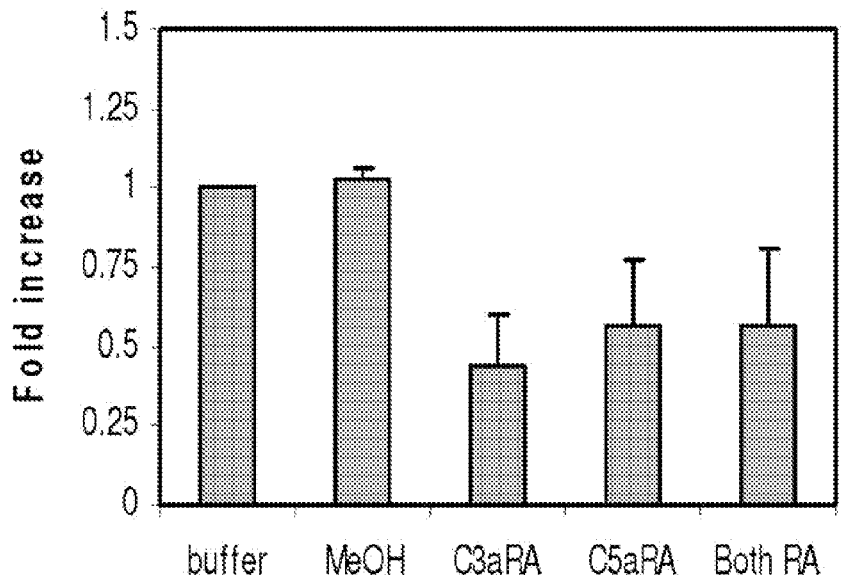
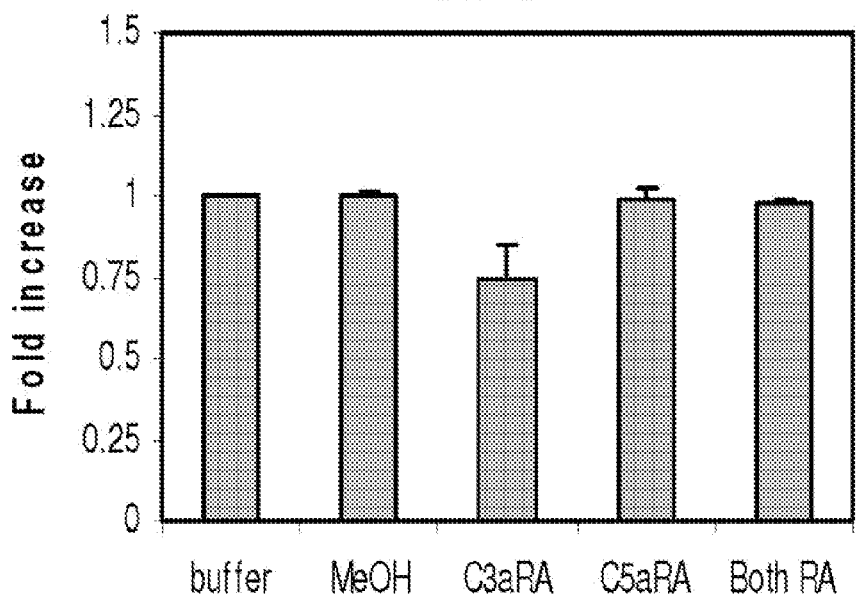
Fig. 10A

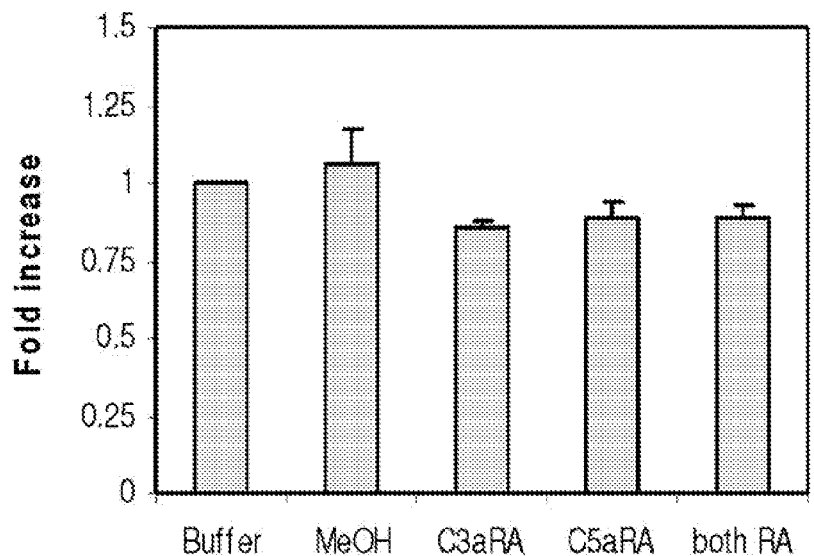
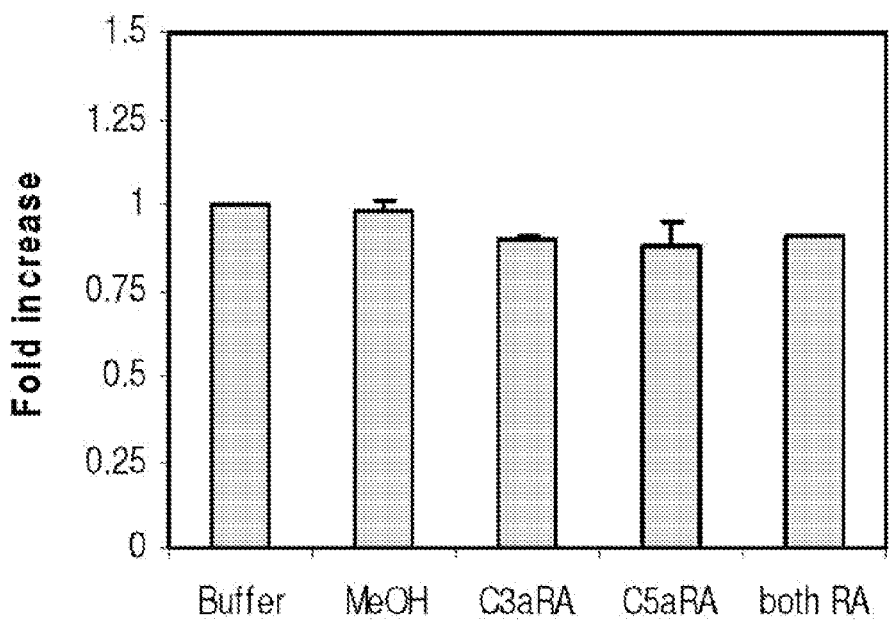
Fig. 10B

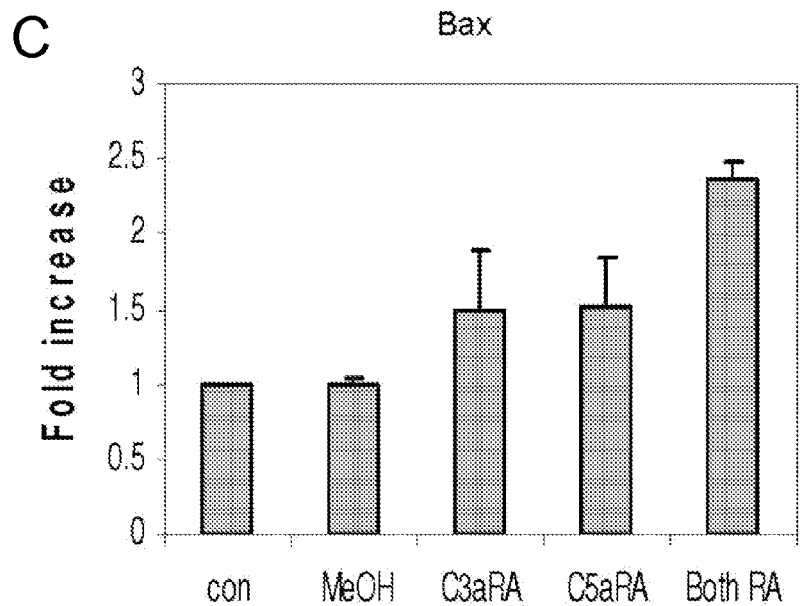
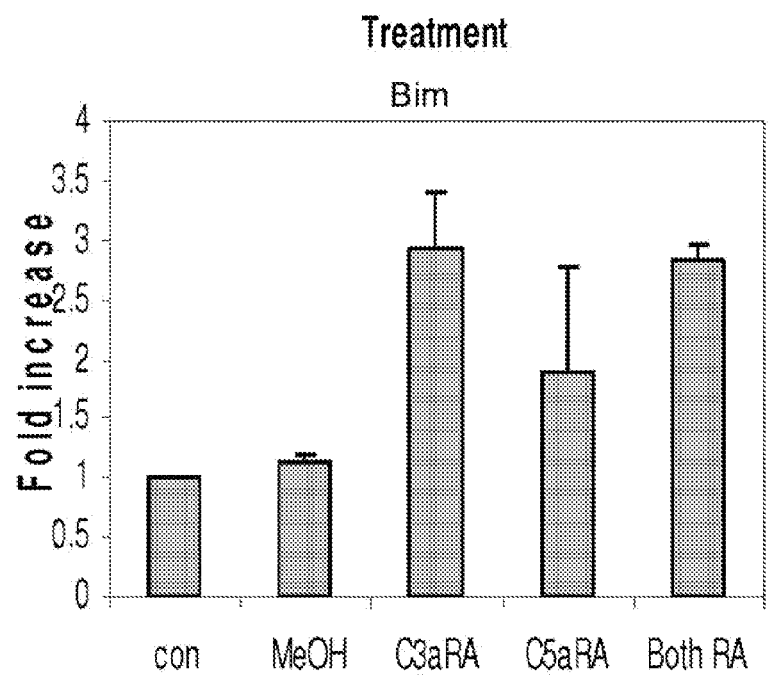
Fig. 10C (Continued)

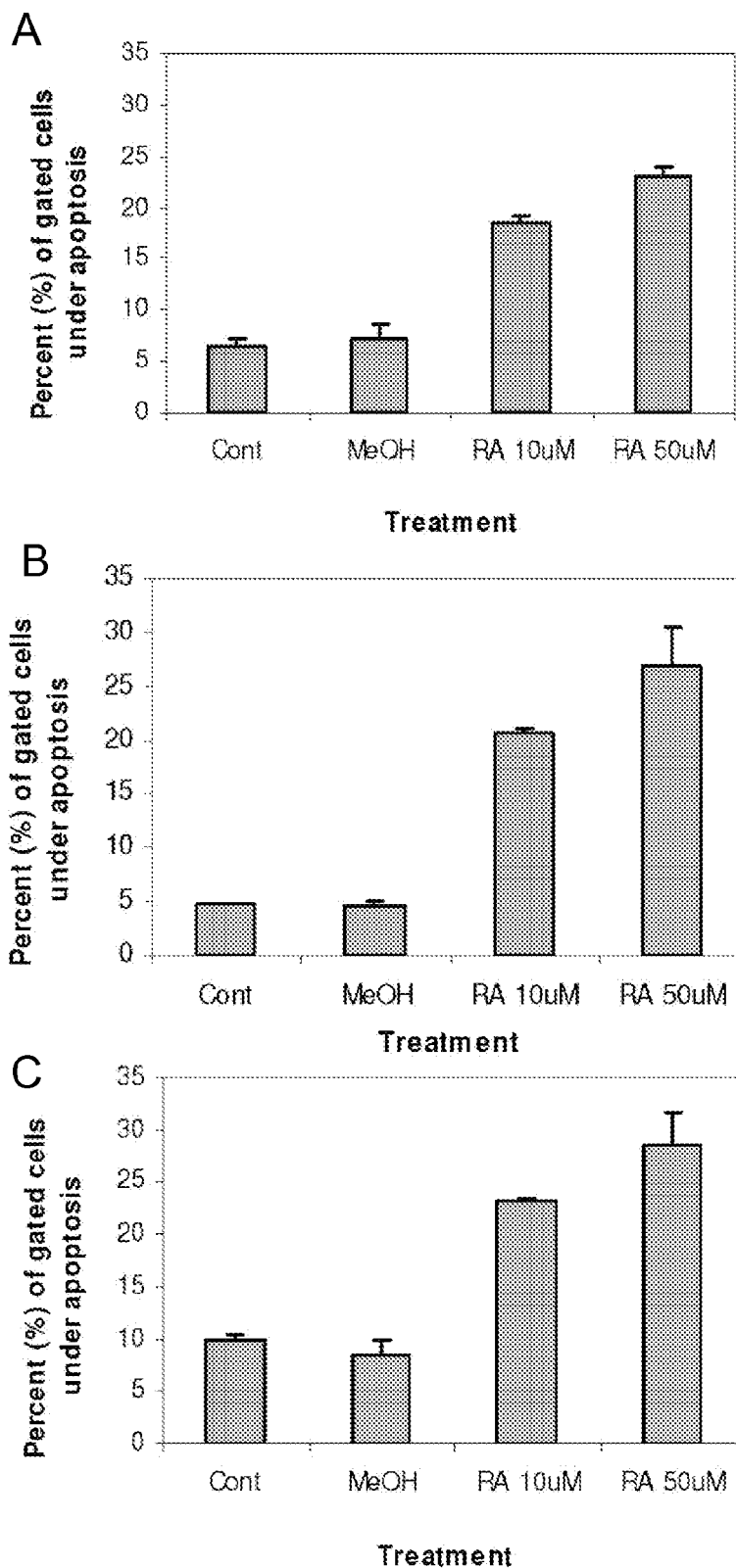
Figs. 12A-C

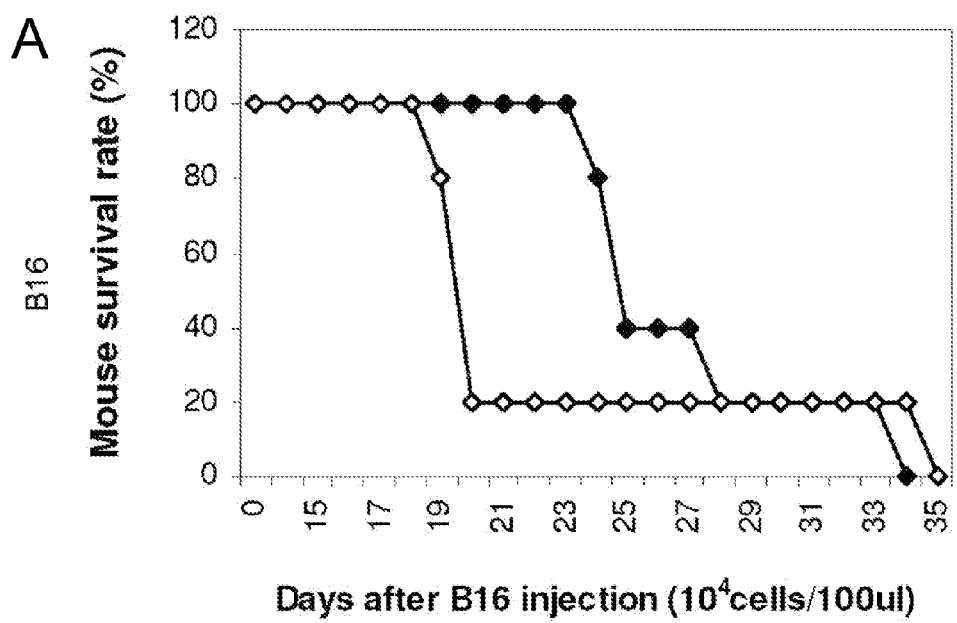
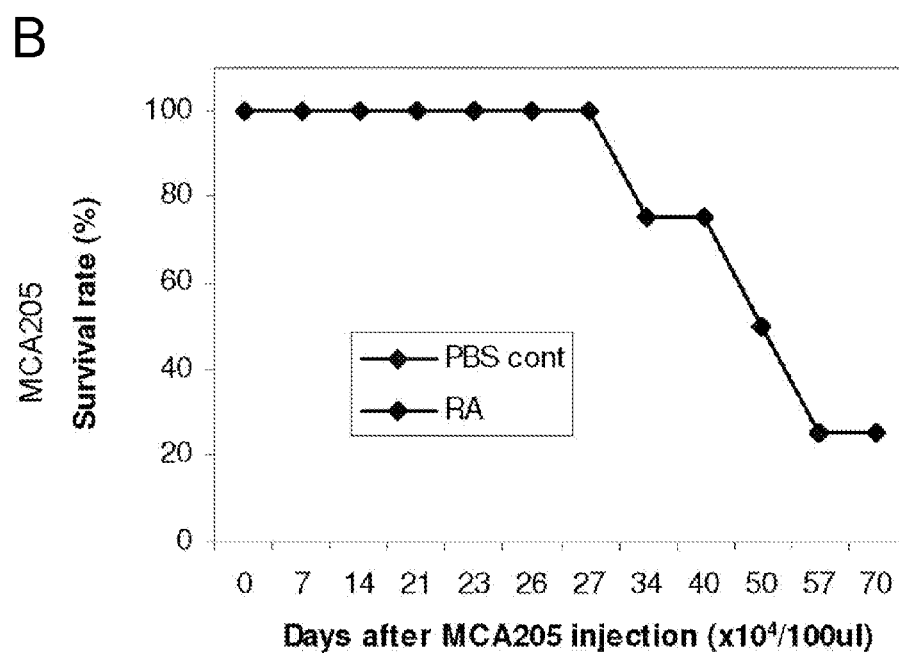
Figs. 13A-B

US 8,940,299 B2

METHOD OF TREATING CANCER

RELATED APPLICATION

This application is a national phase of PCT/US09/035722, filed Mar. 2, 2009, which claims the benefit of U.S. Provisional Application No. 61/032,330, filed Feb. 28, 2008, the subject matter, of which is incorporated herein by reference in its entirety.

TECHNICAL FIELD

The present invention relates generally to a method of inducing apoptosis in neoplastic cells, and more particularly to a method of treating cancer.

BACKGROUND OF THE INVENTION

Research has shown that decay accelerating factor (DAF) and other intrinsic complement regulatory proteins serve as shields to protect self cells from autologous complement-mediated injury. Additionally, research has shown that C5a and C3a receptors (i.e., C5aR and C3aR) play an important role in the attraction of phagocytic cells to immunologically engaged tumor beds and ingestion of complement opsonized tumor cells. Based on these findings, current approaches towards cancer therapy focus on blocking the activities of DAF and other intrinsic regulators so as to render tumors cells susceptible to killing, and on enhancing C5a-C5aR and C3a-C3aR interactions on phagocytic cells so as to increase their influx into tumor beds.

SUMMARY OF THE INVENTION

The present invention relates to a method for inducing apoptosis in a neoplastic cell (e.g., cancer cell or tumor cell) that expresses at least one of C5aR or C3aR. The method includes administering at least one complement antagonist to the cell so that the at least one complement antagonist substantially reduces or inhibits the activity of protein kinase B (PKB) in the cell.

Another aspect of the present invention relates to a method of treating cancer in a subject. The method includes administering to the subject a therapeutically effective amount of at least one complement antagonist so that the at least one complement antagonist substantially reduces or inhibits the activity of PKB in the subject.

A further aspect of the invention relates to a method of treating cancer in a subject by administering to cancer cells expressing C3aR and/or C5aR of the subject a therapeutically effective amount of at least one complement antagonist that substantially reduces or inhibits the interaction of at least one of C3a or C5a with the C3a receptor (C3aR) and C5a receptor (C5aR).

Yet another aspect of the invention relates to a method of treating cancer in a subject by administering to cancer cells expressing C3aR and/or C5aR of the subject a therapeutically effective amount of at least one complement antagonist antibody directed against at least one of C3, C5, C3 convertase, C5 convertase, C3a, C5a, C3aR, or C5aR.

Another aspect of the invention relates to a method of reducing metastases of cancer cells expressing C3aR and/or C5aR of a subject by administering to the cancer cells a therapeutically effective amount of at least one complement antagonist that reduces or substantially inhibits the interaction of at least one of C3a or C5a with the C3a receptor (C3aR) and C5a receptor (C5aR).

BRIEF DESCRIPTION OF THE DRAWINGS

FIG. 6 illustrates C5aR and C3aR Ligation Activates PI3-Kγ, which in turn promotes AKT Phosphorylation. (A) The left side shows that WT T cells were activated with anti-CD3+anti-CD28, and at progressively increasing times, buffer, C5aR-A, or C5aRA+C3aR-A were added; extracts were analyzed for phospho-Ser$^{473}$ AKT by Luminex assays (representative of two experiments). (p<0.05). The right side shows that naive WT and C5ar1$^{−/−}$ C3ar1$^{−/−}$ T cells were incubated with 1 μg/ml of anti-CD3+anti-CD28 at 37° C. and phospho-Ser$^{473}$ AKT assessed at increasing times. (B) WT T cells were incubated at 37° C. with anti-CD3+anti-CD28 (1 μg/ml each) for 3 min after which the cells were incubated for 20 min with buffer or 0.1 μM PI-3Kγ-specific inhibitor PI-103. Extracts were immunoblotted with anti-phospho-Ser$^{473}$ AKT or total AKT mAb (representative of five experiments). (C) OT-II T cells were incubated with 0.1 μM OVA$_{323-339}$, WT DCs, and 0.1 μM PI-103±10 ng/ml C5a. Complement, IL-2, and IFNγ mRNAs were quantitated by qPCR. All error bars are ±SD.

FIG. 12 illustrates an appearance of PCD markers by the acquisition of Annexin V. Cells (5×10$^5$ cells/well) incubated with receptor antagonist were stained annexinV-FITC and their apoptotic activity was analyzed by flow. Graph summarizes apoptotic activity, as determined by the Annexin V-FITC assay, in the presence of either C5a- or C3a-receptor antagonist alone or both. Percent of gated cells under apoptosis in (a) B16, (b) MAC 205 (c) E0771 were 2.5-3 fold higher than control in a concentration and time dependent manner. Data shown are means±standard deviations.

DETAILED DESCRIPTION

Figure 1:
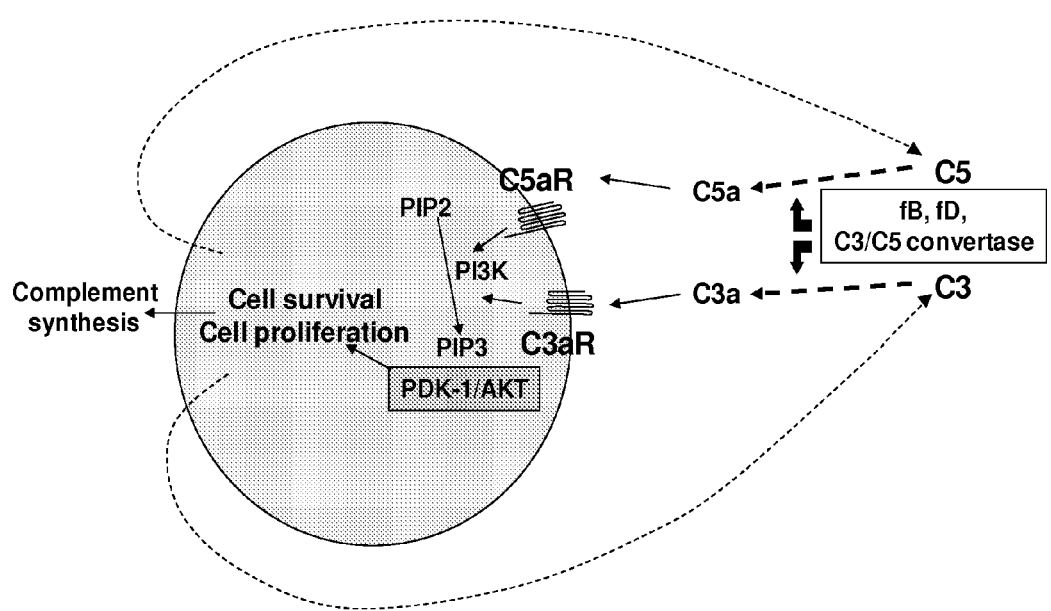
FIG. 1 is a schematic view of the relation between complement components and cancer cell survival/proliferation in accordance with an aspect of the invention.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

In the context of the present invention, the term "polypeptide" refers to an oligopeptide, peptide, or protein sequence, or to a fragment, portion, or subunit of any of these, and to naturally occurring or synthetic molecules. The term "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs and the like, glycosylated polypeptides, and all "mimetic" and "peptidomimetic" polypeptide forms.

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, siRNAs, microRNAs, and ribonucleoproteins. The term also encompasses nucleic acids, i.e., oligonucleotides, containing known analogues of natural nucleotides, as well as nucleic acid-like structures with synthetic backbones.

As used herein, the term "antibody" refers to whole antibodies, e.g., of any isotype (IgG, IgA, IgM, IgE, etc.), and includes fragments thereof which are also specifically reactive with a target polypeptide. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain polypeptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term "antibody" also includes polyclonal, monoclonal, or other purified preparations of antibodies, recombinant antibodies, monovalent antibodies, and multivalent antibodies. Antibodies may be humanized, and may further include engineered complexes that comprise antibody-derived binding sites, such as diabodies and triabodies.

As used herein, the term "complementary" refers to the capacity for precise pairing between two nucleobases of a polynucleotide and its corresponding target molecule. For example, if a nucleobase at a particular position of a polynucleotide is capable of hydrogen bonding with a nucleobase at a particular position of a target polynucleotide (the target nucleic acid being a DNA or RNA molecule, for example), then the position of hydrogen bonding between the polynucleotide and the target polynucleotide is considered to be complementary. A polynucleotide and a target polynucleotide are complementary to each other when a sufficient number of complementary positions in each molecule are occupied by nucleobases which can hydrogen bond with each other. Thus, "specifically hybridizable" and "complementary" are terms which can be used to indicate a sufficient degree of precise pairing or complementarity over a sufficient number of nucleobases such that stable and specific binding occurs between a polynucleotide and a target polynucleotide.

As used herein, the terms "effective," "effective amount," and "therapeutically effective amount" refer to that amount of a complement antagonist and/or a pharmaceutical composition thereof that results in amelioration of symptoms or a prolongation of survival in a subject with cancer. A therapeutically relevant effect relieves to some extent one or more symptoms of cancer, or returns to normal either partially or completely one or more physiological or biochemical parameters associated with or causative of the cancer.

As used herein, the term "subject" refers to any warm-blooded organism including, but not limited to, human beings, rats, mice, dogs, goats, sheep, horses, monkeys, apes, rabbits, cattle, etc.

As used herein, the terms "complement polypeptide" or "complement component" refer to a polypeptide (or a polynucleotide encoding the polypeptide) of the complement system that functions in the host defense against infections and in the inflammatory process. Complement polypeptides constitute target substrates for the complement antagonists provided herein.

As used herein, the term "complement antagonist" refers to a polypeptide, polynucleotide, or small molecule capable of substantially reducing or inhibiting the activity of a complement component.

A complement component can include any one or combination of interacting blood polypeptides or glycoproteins. There are at least 30 soluble plasma polypeptides, in addition to cell surface receptors, which can bind complement reaction products and which can occur on inflammatory cells and cells of the immune system. In addition, there are regulatory membrane proteins that can protect host cells from accidental complement attack. Complement components can include polypeptides that function in the classical pathway, such as C2, polypeptides that function in the alternative pathway, such as Factor B, and polypeptides that function in the lectin pathway, such as MASP-1.

Complement components can also include: any of the "cleavage products" (also referred to as "fragments") that are formed upon activation of the complement cascade; complement polypeptides that are inactive or altered forms of complement polypeptides, such as iC3 and C3a-desArg; and components indirectly associated with the complement cascade. Examples of such complement components can include, but are not limited to, C1q, C1r, C1s, C2, C3, C3a, C3b, C3c, C3dg, C3g, C3d, C3f, iC3, C3a-desArg, C4, C4a, C4b, iC4, C4a-desArg, C5, C5a, C5a-des-Arg, C6, C7, C8, C9, MASP-1, MASP-2, MBL, Factor B, Factor D, Factor H, Factor I, CR1, CR2, CR3, CR4, properdin, C1Inh, C4bp, MCP, DAF, CD59 (MIRL), clusterin, HRF, and allelic and species variants of any complement polypeptide.

As used herein, the terms "cancer," and "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, breasts, prostate, ovaries, colon, kidneys, cervix and liver.

As used herein, the terms "cancer cell" or "tumor cell" refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, chorioc arcinoma, semonoma, embryonal carcinoma, mammary carcinomas, gastrointestinal carcinoma, colonic carcinomas, bladder carcinoma, prosta to carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma.

The present invention relates generally to immunotherapy, and more particularly to a method of treating neoplastic disorders, such as tumors and cancer, using complement antagonists. Referring to FIG. 1, it was discovered that cancer cells (e.g., melanoma cells, fibrosarcoma cells, breast cancer cells, cervical cancer cells, and leukemia cells) can express C3a and C5a receptors (i.e., C3aR and C5aR) as well as endogenously produce C3 and C5. C3 convertase and C5 convertase in the supernatant can cleave endogenously produced C3 and C5, as well as systemic C3 and C5, to form complement anaphylatoxins C3a and C5a. C3aR and C5aR are G protein coupled receptors (GPCRs). Interactions of C3a and C5a with their receptors, C3aR and C5aR, on cancer cells were found to be integrally involved in cancer cell proliferation and survival.

Figure 2C:
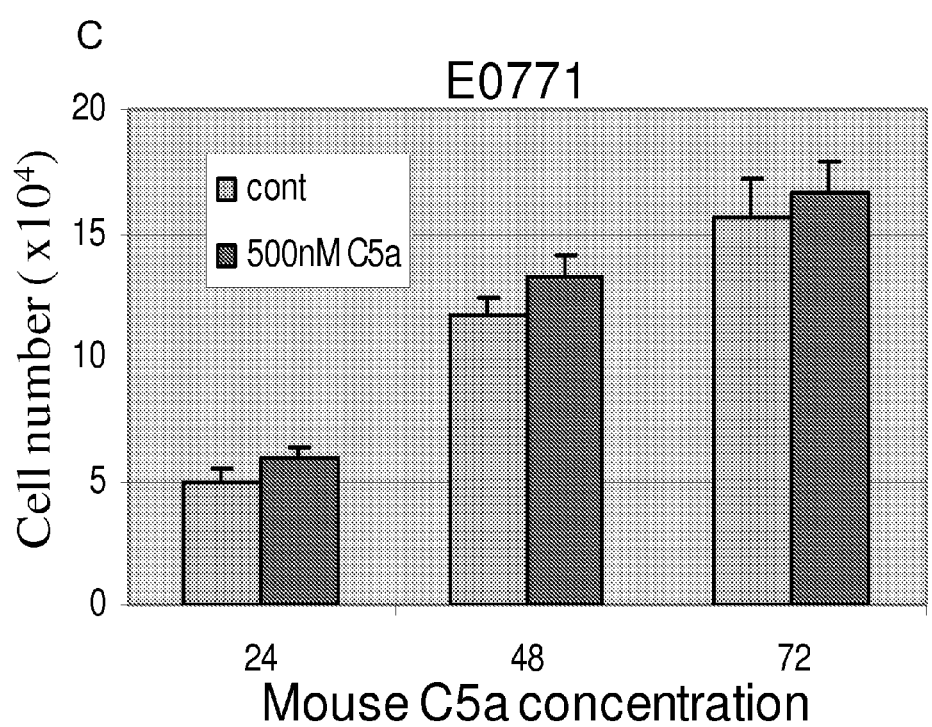
FIG. 2 illustrates graphs showing cell growth in 3 cancer cell lines (a) MCA 205 (fibrosarcoma), (b) B16 (melanoma cell), and (c) E0771 (breast cancer) after mouse C5a treatment in Opti-MEM media (serum-reduced media).
Figure 3:
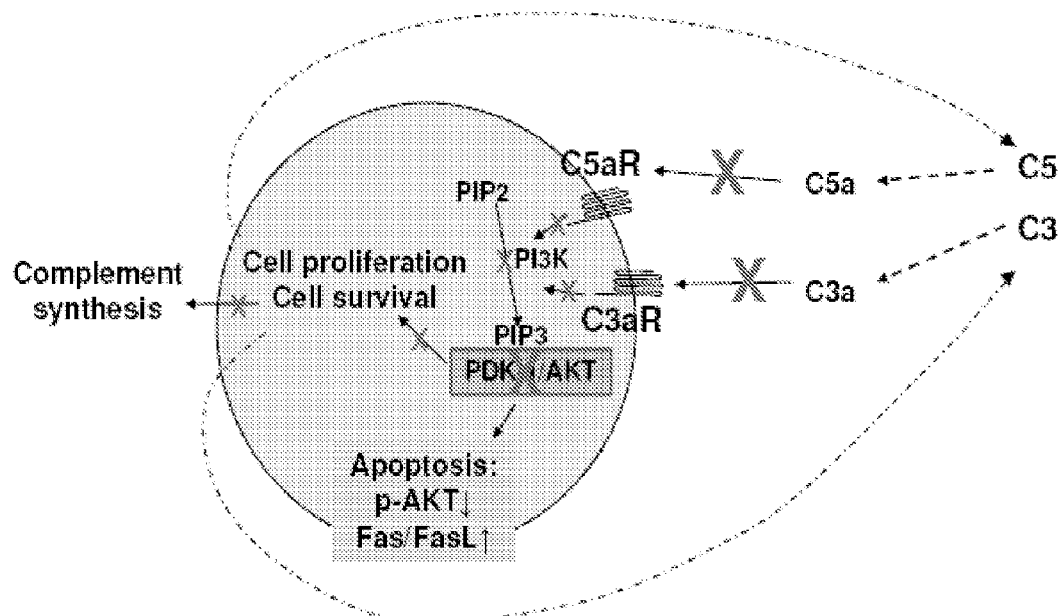
FIG. 3 is a schematic view of the strategy to inhibit cancer cell survival/proliferation in accordance with an aspect of the invention.

It is believed that C3aR and C5aR GPCR signal transduction resulting from interaction with local C5a and C3a is essential for AKT phosphorylation (also known as protein kinase B or PKB) in the cancer cells. AKT phosphorylation can promote proliferation and survival to the cancer cells. For example, FIG. 2 shows that C5a enhances cell survival in three cancer cell lines. Unexpectedly, it was found that blocking C5a/C3a-C5aR/C3aR interactions in cancer cells decreases cell proliferation and induces cell death. It is believed as shown schematically in FIG. 3 that if C5a/C3a-C5aR/C3aR interactions in cancer cells are interrupted, phosphorylated AKT, an intermediate that suppresses apoptosis, cannot be produced and induces cell death. Additionally, interruption of C5a/C3a-C5aR/C3aR interactions induces Fas/FasL surface expression and down regulates Bcl-2/Bcl-xl transcripts and reciprocal up-regulation of Bax/Bim transcripts of the neoplastic cells, which can promote cell death. Further, interruption of C5a/C3a-C5aR/C3aR interactions can inhibit EGFR and IGFR phophorylation, which can substantially inhibit and/or reduce EGF and IGF induced proliferation and matastases of the neoplastic cells.

As shown in the Examples of the present application, it was found in studies with cancer cells (e.g., melanoma, fibrosarcoma, breast cancer, cervical cancer, and leukemia cell lines) that blocking C5a/C3a-C5aR/C3aR interactions using either C5aR and C3aR antagonists or adding antagonists (e.g., mAbs) to their C5a and C3a ligands reduces proliferation and kills the cancer cells. This shows that complement antagonists (e.g., competitive inhibitors, mABs, interfering RNA) used in combination will not only suppress expansion of cancer or tumor cells in patients but eliminate the cancer cells by virtue of inducing apoptosis. Based on these discoveries, the present invention provides a method for inducing apoptosis in a neoplastic cell (e.g., tumor cell or cancer cell) and a method for treating a neoplastic disorder (e.g., cancer) in a subject.

The method of the present invention can include administering to a neoplastic cell (e.g., cancer cell or tumor cell) that expresses at least one of C5aR or C3aR at least one complement antagonist that inhibits or substantially reduces activity of a complement component and substantially reduces or inhibits the activity of PKB in the cell. By inhibiting or substantially reducing the activity of a complement component, it is meant that the activity of the complement component may be entirely or partly diminished. For example, an inhibition or reduction in the functioning of a C3/C5 convertase may prevent cleavage of C5 and C3 into C5a and C3a, respectively. An inhibition or reduction in the functioning of C5, C3, C5a and/or C3a polypeptides may reduce or eliminate the ability of C5a and C3a to bind C5aR and C3aR, respectively. An inhibition or reduction in Factor B, Factor D, properidin, Bb, Ba and/or any other protein of the complement pathway that is used in the formation of C3 convertase, C5 convertase, C5, C3, C5a and/or C3a may reduce or eliminate the ability of C5a and C3a to be formed and bind to C5aR and C3aR, respectively. Additionally, an inhibition or reduction in the functioning of a C5aR or C3aR may similarly reduce or eliminate the ability of C5a and C3a to bind C5aR and C3aR, respectively.

Figure 4:
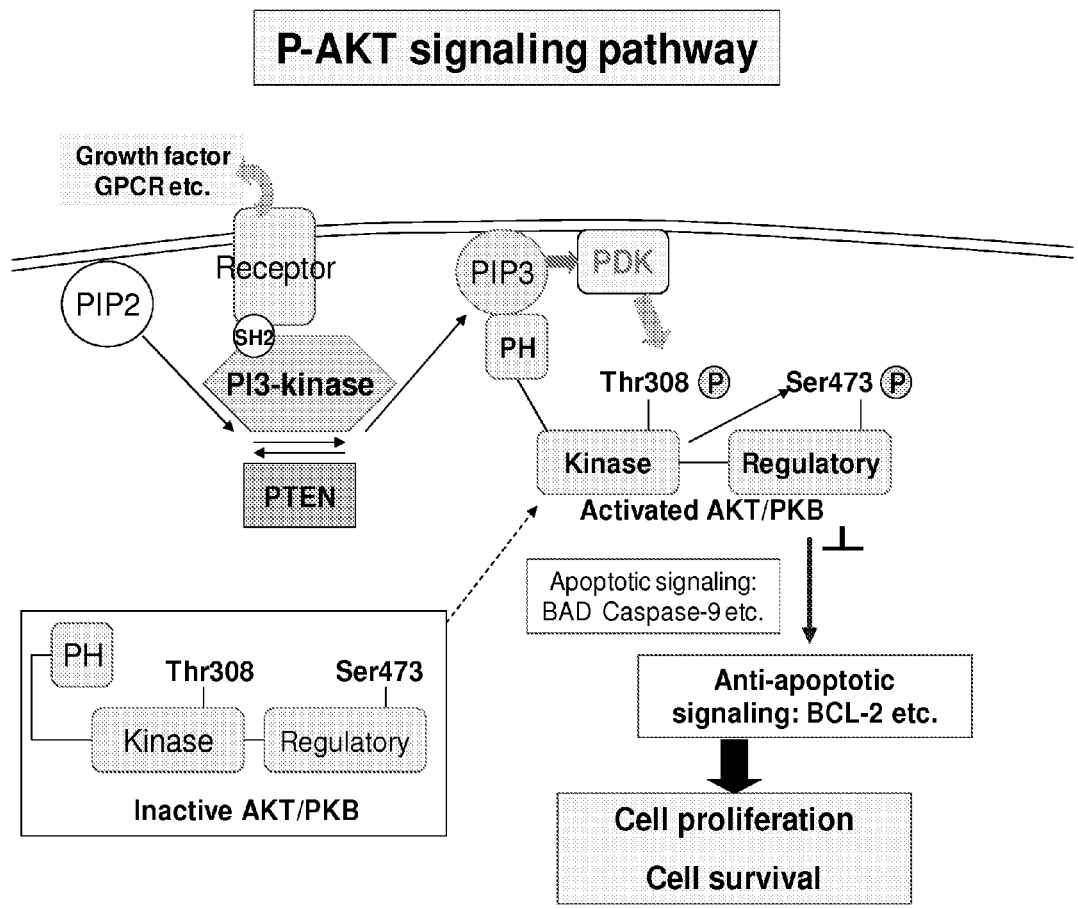
FIG. 4 is a schematic view of the P-AKT signaling pathway.

A partial or entire reduction in the activity of a complement component can substantially reduce or eliminate the activity of PKB in the cell. As discussed above, PKB is one component of the AKT signaling pathway. In the AKT signaling pathway as shown schematically in FIG. 4, a polypeptide, such as C3a or C5a, can first bind to a membrane receptor. Binding of the polypeptide activates PI-3K which, in turn, can convert PIP2 to PIP3. PIP3 can then activate the kinase PDK1 which, in turn, can activate PKB. Proteins phosphorylated by activated AKT can promote cell survival. For example, phosphorylation of PIkappa-B kinase can lead to the activation of NF-kB to oppose apoptosis. Additionally, phosphorylation of Bad, a protein in the Bcl-2 gene family that opposes Bcl-2, by AKT can block anti-apoptotic activity and promote cell survival. Similarly, phosphorylation of the protease caspase 9 (or forkhead) transcription factors by AKT can block the induction of apoptosis by these factors. A substantial reduction in the AKT signaling pathway by the administration of complement antagonist to a neoplastic cells of a subject can, however, reduce cell proliferation and induce programmed cell death.

In an aspect of the invention, the at least one complement antagonist can include an antibody or antibody fragment directed against a complement component that can affect or inhibit the formation of C3a and/or C5a (e.g., anti-Factor B, anti-Factor D, anti-C5, anti-C3, ant-C5 convertase, and anti-C3 convertase) and/or reduce C5a/C3a-C5aR/C3aR interactions (e.g., anti-C5a, anti-C3a, anti-C5aR, and C3aR antibodies). In one example of the present invention, the antibody or antibody fragment can be directed against or specifically bind to an epitope, an antigenic epitope, or an immunogenic epitope of a C5, C3, C3a, C5a, C5aR, C3aR, C5 convertase, and/or C3 convertase. The term "epitope" as used herein can refer to portions of C5, C3, C3a, C5a, C5aR, C3aR, C5 convertase, and/or C3 convertase having antigenic or immunogenic activity. An "immunogenic epitope" as used herein can include a portion of a C5, C3, C3a, C5a, C5aR, C3aR, C5 convertase, and/or C3 convertase that elicits an immune response in a subject, as determined by any method known in the art. The term "antigenic epitope" as used herein can include a portion of a polypeptide to which an antibody can immunospecifically bind as determined by any method well known in the art.

Examples of antibodies directed against C5, C3, C3a, C5a, C5aR, C3aR, C5 convertase, and/or C3 convertase are known in the art. For example, mouse monoclonal antibodies directed against C3aR can include those available from Santa Cruz Biotechnology, Inc. (Santa Cruz, Calif.). Monoclonal anti-human C5aR antibodies can include those available from Research Diagnostics, Inc. (Flanders, N.J.). Monoclonal anti-human/anti-mouse C3a antibodies can include those available from Fitzgerald Industries International, Inc. (Concord, Me.). Monoclonal anti-human/anti-mouse C5a antibodies can include those available from R&D Systems, Inc. (Minneapolis, Minn.).

In another aspect of the invention, the complement antagonist can include purified polypeptide that is a dominant negative or competitive inhibitor of C5, C3, C3a, C5a, C5aR, C3aR, C5 convertase, and/or C3 convertase. As used herein, "dominant negative" or "competitive inhibitor" refers to variant forms of a protein that inhibit the activity of the endogenous, wild type form of the protein (i.e., C5, C3, C3a, C5a, C5aR, C3aR, C5 convertase, and/or C3 convertase). As a result, the dominant negative or competitive inhibitor of a protein promotes the "off" state of protein activity. In the context of the present invention, a dominant negative or competitive inhibitor of C5, C3, C3a, C5a, C5aR, C3aR, C5 convertase, and/or C3 convertase is a C5, C3, C3a, C5a, C5aR, C3aR, C5 convertase, and/or C3 convertase polypeptide, which has been modified (e.g., by mutation of one or more amino acid residues, by posttranscriptional modification, by posttranslational modification) such that the C5, C3, C3a, C5a, C5aR, C3aR, C5 convertase, and/or C3 convertase inhibits the activity of the endogenous C5, C3, C3a, C5a, C5aR, C3aR, C5 convertase, and/or C3 convertase.

In an aspect of the invention, the competitive inhibitor of C5, C3, C3a, C5a, C5aR, C3aR, C5 convertase, and/or C3 convertase can be a purified polypeptide that has an amino acid sequence, which is substantially similar (i.e., at least about 75%, about 80%, about 85%, about 90%, about 95% similar) to the wild type C5, C3, C3a, C5a, C5aR, C3aR, C5 convertase, and/or C3 convertase but with a loss of function. The purified polypeptide, which is a competitive inhibitor of C5, C3, C3a, C5a, C5aR, C3aR, C5 convertase, and/or C3 convertase, can be administered to a neoplastic cell (e.g., cancer cell or tumor) expressing C5aR and/or C3aR, such as a melanoma cell, leukemia cell, fibrosarcoma cell, cervical cancer cell, breast cancer cell, etc., to reduce cell proliferation and induce cell death.

It will be appreciated that antibodies directed to other complement components used in the formation of C5, C3, C5a, C3a, C5 convertase, and/or C3 convertase can be used in accordance with the method of the present invention to reduce and/or inhibit interactions C5a and/or C3a with C5aR and C3aR on the cancer cells. The antibodies can include, for example, known Factor B, properdin, and Factor D antibodies that reduce, block, or inhibit the classical and/or alternative pathway of the complement system.

In a further aspect of the present invention, the at least one complement antagonist can include RNA interference (RNAi) polynucleotides to induce knockdown of an mRNA encoding a complement component. For example, an RNAi polynucleotide can comprise an siRNA capable of inducing knockdown of an mRNA encoding a C3, C5, C5aR, or C3aR polypeptide in the neoplastic cell.

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (I) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et a 1. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Examples of a siRNA molecule directed to an mRNA encoding a C3a, C5a, C5aR, or C3aR polypeptide are known in the art. For instance, human C3a, C3aR, and C5a siRNA is available from Santa Cruz Biotechnology, Inc. (Santa Cruz, Calif.). Additionally, C5aR siRNA is available from Qiagen, Inc. (Valencia, Calif.). siRNAs directed to other complement components, including C3 and C5, are known in the art.

In other embodiments, the RNAi construct can be in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects, which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid can be used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Examples RNAi constructs that specifically recognize a particular gene or a particular family of genes, can be selected using methodology outlined in detail above with respect to the selection of antisense oligonucleotide. Similarly, methods of delivery RNAi constructs include the methods for delivery antisense oligonucleotides outlined in detail above.

In some embodiments, a lentiviral vector can be used for the long-term expression of a siRNA, such as a short-hairpin RNA (shRNA), to knockdown expression of C5, C3, C5aR, and/or C3aR in cancer cells. Although there have been some safety concerns about the use of lentiviral vectors for gene therapy, self-inactivating lentiviral vectors are considered good candidates for gene therapy as they readily transfect mammalian cells.

It will be appreciated that RNAi constructs directed to other complement components used in the formation of C5, C3, C5a, C3a, C5 convertase, and/or C3 convertase can be used in accordance with the method of the present invention to reduce and/or inhibit interactions C5a and/or C3a with C5aR and C3aR on the cancer cells. The RNAi constructs can include, for example, known Factor B, properdin, and Factor D siRNA that reduce expression of Factor B, properdin, and Factor D.

Moreover, it will be appreciated that other antibodies, small molecules, and/or peptides that reduce or inhibit the formation of C5, C3, C5a, C3a, C5 convertase, and/or C3 convertase and/or that reduce or inhibit interactions C5a and/or C3a with C5aR and C3aR on the cancer cells can be used as a complement antagonist in accordance with the method of the present invention. These other complement antagonists can be administered to the subject and/or cancer cells at amount effective to reduce PKB phosphorylation in the cells. Example of such other complement antagonists include C5aR antagonists, such as AcPhe[Orn-Pro-D-cyclohexylalanine-Trp-Arg, prednisolone, and infliximab (Woodruff et al., *The*

*Journal of Immunology,* 2003, 171: 5514-5520), hexapeptide MeFKPdChaWr (March et al., *Mol Pharmacol* 65:868-879, 2004), PMX53 and PMX205, and N-[(4-dimethylaminophenyl)methyl]-N-(4-isopropylphenyl)-7-methoxy-1,2,3,4-tetrahydronaphthalen-1-carboxamide hydrochloride (W-54011) (Sumichika et al., J. Biol. Chem., Vol. 277, Issue 51, 49403-49407, Dec. 20, 2002), and a C3aR antagonist, such as SB 290157 (Ratajczak et al., Blood, 15 Mar. 2004, Vol. 103, No. 6, pp. 2071-2078).

The at least one complement antagonist can be administered to the neoplastic cells (e.g., cancer cells or tumor cells), either in vivo or in vitro. The cell can be derived from a human subject, from a known cell line, or from some other suitable source. One example of a cell can include a cancerous lymphocyte located in, for example, a human subject. The cell may be isolated or, alternatively, associated with any number of identical, similar, or different cell types. Where the cell comprises a lymphocyte, for example, the lymphocyte may be associated with a costimulatory cell, such as an APC. The neoplastic cell can also comprise a cancer cell in the subject and the complement antagonist can be used to treat cancer in the subject. The at least one complement antagonist can be administered to the treat the cancer in the subject using any one or combination of known techniques.

In one aspect of the invention, the complement antagonist can be administered directly or locally to cells of a cancer or tumor by, for example, direct injection of the complement antagonist into the cancer or tumor site, the supernatant of the cancer or tumor, and/or about the periphery of the cancer or tumor site. Local or direct administration of the complement antagonist into and/or about the periphery of the cancer or tumor site is advantageous because the complement antagonist localizes at the cancer or tumor being treated and does not substantially affect the subject's innate complement system.

In another aspect of the invention, the complement antagonist can be administered to the subject systemically by, for example, intravenous, intraarterial, intraperitoneal, intramuscular, subcutaneous, intrapleural, intrathecal, oral or nasal route, to treat the cancer or tumor in the subject. When administered systemically, the complement antagonist is preferably targeted to the cancer or tumor cells to ensure that the complement antagonist is delivered to the tumor cells or cancer cells, does not adversely affect other normal cells expressing C5aR and/or C3aR, and to potentially mitigate adverse systemic effects on the subject's complement system. Several systems have been developed in order to restrict the delivery of the complement antagonist to the cancer or tumor site. With the identification of cells specific receptors and antigens on cancers or tumor cells, it is possible to actively target the complement antagonist using ligand or antibody bearing delivery systems. Alternatively, the complement antagonist can be loaded on a high capacity drug carriers, such as liposomes or conjugated to polymer carriers that are either directly conjugated to targeting proteins/peptides or derivatised with adapters conjugated to a targeting moiety.

Examples of antibodies active against neoplasia and which can be potentially conjugated to the complement antagonist to target the complement antagonist to the tumor site or cancer include, but are not limited to, anti-cancer antibodies such as 1D09C3, Abciximab, Alemtuzumab, Apolizumab, Avastin, Basiliximab, Bevacizumab, Cantuzumab, Cetuximab, Dacliximab, Eculizumab, Epratuzumab, Gemtuzumab Ozogamicin, Ibritumomab Tiuxetan, Infliximab, Labetuzumab, Mapatumumab, Matuzumab, Mepolizumab, Muromonab-Cd3, Nimotuzumab, Oregovomab, Palivizumab, Panitumumab, Panorex, Pertuzumab, Rituximab, Tositumomab, and Trastuzumab. Other antibodies that can be used are anti-CD20 antibodies (e.g., Rituxan, Bexxar, Zevalin), anti-Her2/neu antibodies (e.g., Herceptin), anti-CD33 antibodies (e.g., Mylotarg), anti-CD52 antibodies (e.g., Campath), anti-CD22 antibodies, anti-CD25 antibodies, anti-CTLA-4 antibodies, anti-EGF-R antibodies (e.g. Erbitux), anti-VEGF antibodies (e.g. Avastin, VEGF Trap) anti-HLA-DR10β antibodies, anti-MUC1 antibodies, anti-CD40 antibodies (e.g. CP-870,893), anti-Treg cell antibodies (e.g. MDX-010, CP-675,206), anti-GITR antibodies, anti-CCL22 antibodies, and the like.

An antibody contemplated herein for targeting includes any antibody specific to any region of a protein involved in the abnormal growth, differentiation, duplication, angiogenesis, metastasis, apoptosis and/or invasion of cells and the like.

The complement antagonist, whether administered locally and/or systemically, can also be provided in a pharmaceutically acceptable composition. The phrase "pharmaceutically acceptable" should be understood to mean a material which is not biologically or otherwise undesirable, i.e., the material may be incorporated into an antiviral composition and administered to a subject without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. Sterile phosphate-buffered saline is one example of a pharmaceutically acceptable carrier. Other suitable carriers are well-known to those in the art. See, for example, REMINGTON'S PHARMACEUTICAL SCIENCES, 19th Ed. (1995), and later editions.

In general, the dosage of the at least one complement antagonist will vary depending upon such factors as the subject's age, weight, height, sex, general medical condition and previous medical history. Typically, it is desirable to provide the subject with a dosage of the at least one complement antagonist which is in the range of from about 1 pg/kg to 10 mg/kg (amount of agent/body weight of patient), although a lower or higher dosage also may be administered as circumstances dictate. The specific dosage or amount of complement antagonist administered to the neoplastic cell (e.g., tumor cells or cancer cell) will be that amount effective reduce PKB activity and to induce apoptosis of the neoplastic cell and/or substantially reduce or inhibit C5/a/C3a-C5aR/C3aR interactions.

In an example of the method, a therapeutically effective amount of a pharmaceutical composition comprising a first antibody directed against C3aR and a second antibody directed against C5aR can be administered to a subject having a lymphoma. The pharmaceutical composition can be administered to the subject intravenously using, for example, a hypodermic needle and syringe. Upon administration of the pharmaceutical composition to the subject, the first and second antibodies can respectively bind to C3aR and C5aR on at least one cancerous lymphocyte. Binding of the first and second antibodies can effectively inhibit or reduce the ability of C3a and C5a to respectively bind C3aR and C5aR. Consequently, the activity of PI-3K in the at least one cancerous lymphocyte may be substantially reduced or inhibited such that PDK cannot activate PKB. In the absence of PKB activation, anti-apoptotic signaling can be reduced or eliminated such that the at least one cancerous lymphocyte undergoes apoptosis.

The following examples are for the purpose of illustration only and are not intended to limit the scope of the claims, which are appended hereto.

EXAMPLE 1

C5a-C5aR+C3a-C3aR Signaling is Linked to T Cell Activation Through PI3-Kg-Induced Phosphorylation of AKT Studies with Jurkat cells have shown that B7-CD28 ligation signals in T cells through phosphorylation of $Y^{170}$ residue in the YMNM motif in CD28's cytoplasmic tail, permitting SH2-dependent binding and activation of PI-3 kinase p85αp110α (PI-3Kα). The activated PI-3Kα increases the amount of internal leaflet-associated phosphatidylinositol 3,4,5 trisphosphate [PtdIns (3,4,5)$P_3$], causing the recruitment of PDK1, PDK2, and AKT via their pleckstrin homology (PH) domains [which enable them to bind PtdIns (3,4,5) $P_3$]. This juxtaposition on PtdIns (3,4,5)$P_3$ allows PDK1+ PDK2 to produce dually $Thr_{308}Ser_{473}$ phosphorylated AKT that is centrally implicated in CD28 costimulatory signaling.

Figure 5B:
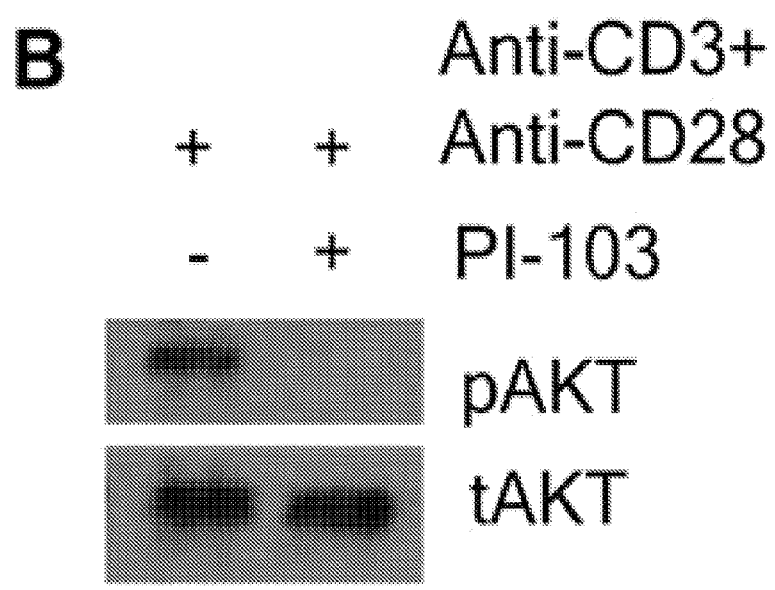
FIG. 5 illustrates immunoblots of A) anti-phospho-Ser473 AKT (rep of 5 exps) of WT T cells incubated with with anti-CD3+anti-CD28±C5aR-A+C3aR-A (10 ng/ml each). B) anti-phospho-Ser473 AKT (rep of 5 exps) of WT or C5ar1−/− C3ar1−/− T cells incubated with anti-CD3+anti-CD28.
Figure 5C:
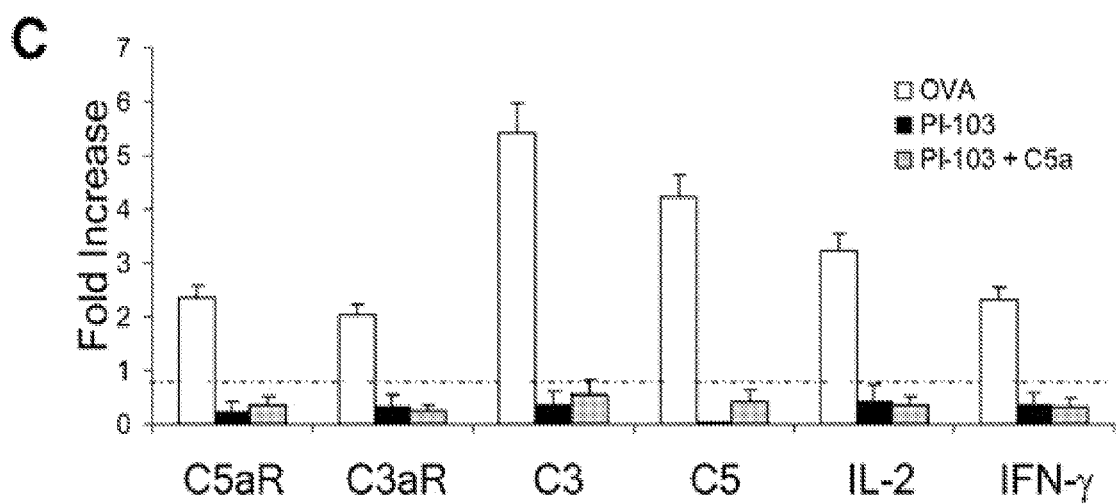

To test whether abrogated CD28 costimulation in the absence or blockade of C5aR+C3aR relates to a requirement for these GCPR signals for optimal AKT phosphorylation, we stimulated WT T cells with anti-CD3+anti-CD28±C5aR-A and C3aR-A and assessed AKT phosphorylation by immunoblotting (FIG. 5A) and Luminex assay (FIG. 6A). Notably, whereas addition of the C5aR-A diminished AKT phosphorylation, both antagonists together virtually abolished it. Moreover, significantly less phosphorylated AKT was detectable upon anti-CD3+anti-CD28 stimulation of $C5ar1^{-/-}$ $C3ar1^{-/-}$ T cells at all time points tested (FIG. 6B).

AKT is one product resulting from the activity of the p110 catalytic subunit of PI-3 kinase p101γp110γ (PI-3Kγ), and PI-3Kγ has been tied to GCPR signal transduction in neutrophils and macrophages. To test whether this signaling pathway is operational in T cells, we incubated WT T cells with anti-CD3+anti-CD28 plus a specific inhibitor (PI-103) of PI-3Kγ. Strikingly, addition of the inhibitor (1) abrogated anti-CD3+anti-CD28-induced phosphorylation of AKT (FIG. 6B), (2) prevented the upregulation of complement gene expression, and (3) eliminated upregulation of IL-2 and IFNγ mRNA expression (FIG. 6C). Consistent with PI-3Kγ activation being mediated through C5aR ligation, these suppressive effects could not be overcome by added C5a (FIG. 6C). Thus, C5aR- and C3aR-induced PI-3Kγ activation is necessary for AKT phosphorylation and resultant T cell activation.

C5aR+C3aR Signaling is Essential for Sustaining Naive T Cell Viability

We detected low levels of C5a+C3a in culture supernatants of T cells in the absence of stimulation (FIG. 7B), a result raising the possibility that C5a+C3a is generated constitutively and is important for T cell function. Moreover, we observed reduced $S^{473}$ AKT phosphorylation at early time points after preincubation of mouse T cells with the C5aR-A and C3aR-A (FIG. 6A and FIG. 5A), further implicating C5a-C5aR+C3a-C3aR interactions as operating tonically in naive T cells. The two results would be consistent with preexisting C5a+C3a feeding back on C5aR+C3aR to trigger ongoing basal GPCR activation. In support of this, C5aR and C3aR could be detected on unstimulated T cells with an ultrabright chromophore, WT but not $C5ar1^{-/-}$ $C3ar1^{-/-}$ T cells produced C5a and C3a at rest (FIG. 7A), and as noted in FIG. 6A, basal phospho $S^{473}$ AKT was readily detectable in WT T cells but was markedly reduced in $C5ar1^{-/-}$ $C3ar1^{-/-}$ T cells (FIG. 6B). Because of the known association of loss of phospho $S^{473}$ AKT with induction of programmed cell death (PCD), this connection of disabled C5aR+C3aR GPCR signaling in naive unstimulated cells with reduced phospho $S^{473}$ AKT suggested the intriguing possibility that in naive T cells, constitutive C5a-C5aR+C3a-C3aR interactions play a role in maintaining viability.

To test this possibility, we compared the survival of WT and $C5ar1^{-/-}$ $C3ar1^{-/-}$ T cells in vitro after 48 hr of incubation in 10% heat-inactivated FCS. These analyses showed that in contrast to about 5% loss of WT T cells, 20%-30% loss of $C5ar1^{-/-}$ $C3ar1^{-/-}$ T cells occurred (FIG. 7A). To eliminate effects of exogenous complement, growth factors, and other agents in serum, we repeated the survival studies with serum-free medium. Fewer surviving $C5ar1^{-/-}$ $C3ar1^{-/-}$ T cells were detected at 6 hr, confirming that disrupted autocrine signaling through both the C5aR and C3aR contributed to the decline (FIG. 7B). To confirm that these effects were not reflective of other processes, we incubated naive WT T cells in serum-free medium containing anti-C3a and/or anti-C5a mAbs against the C5aR+C3aR ligands rather than blocking the receptors themselves (FIG. 7C). This caused a diminution in cell numbers similar to that observed with $C5ar1^{-/-}$ $C3ar1^{-/-}$ cells. As yet another test, we added C5a to C5-deficient or $C3^{-/-}$ T cells. This augmented 6 hr viability of both knockouts by ~25%, close to the viability of WT cells (FIG. 7D). Thus, tonic C5a-C5aR+C3a-C3aR signal transduction is necessary for maintaining T cells in a viable state.

Figure 7F:
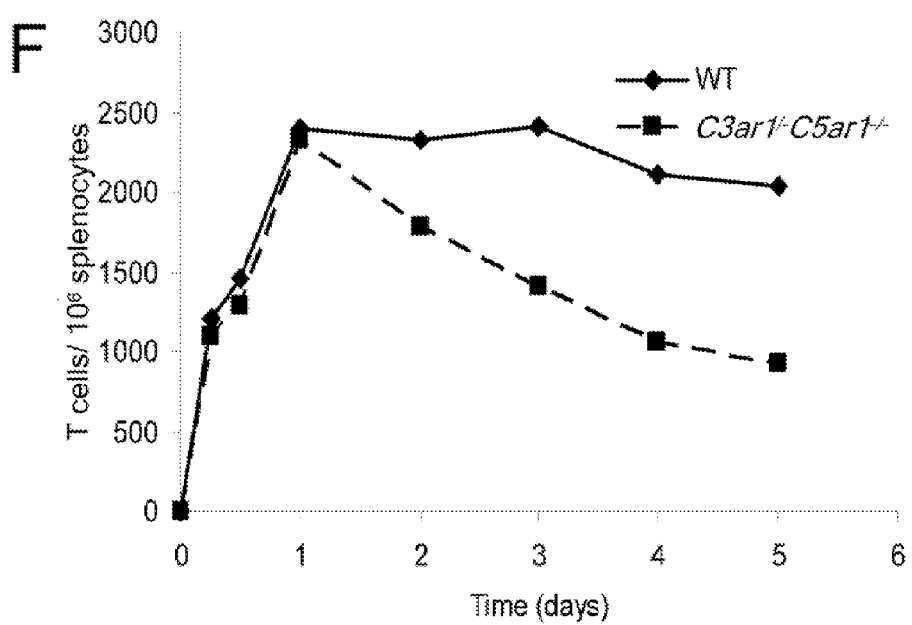
FIG. 7 illustrates constitutive C5a and C3a Production and Signaling via the C5aR and C3aR GPCRs Influences Cell Viability In Vitro and In Vivo. (A) The left side shows that WT T cells were stained with Alexa647-labeled Ab for detection of C3aR and C5aR expression in resting T cells. The center shows that WT T cells were incubated at 37° C. for 17 hr, supernatants were concentrated 10-fold, and C3a or C5a were immunoblotted. The right side shows that WT and C5ar1$^{−/−}$ C3ar1$^{−/−}$ T cells were incubated in complete RPMI 1640 and viability assessed as described in the Experimental Procedures (representative of three experiments). (B) WT and C5ar1$^{−/−}$, C3ar1$^{−/−}$, and C5ar1$^{−/−}$ C3ar1$^{−/−}$ T cells were incubated for 6 hr in serum-free HL-1 medium and viability assayed. (C) WT T cells were incubated at 37° C. for 6 hr in HL-1 medium±anti-C3a, anti-C5a, or anti-C3a+anti-C5a and viability assessed. (D) C3$^{−/−}$ and C5-deficient T cells were incubated for 6 hr in HL-1 medium±300 ng/ml C5a added at time 0 and 90 min (E) Spleens from naive WT, C3ar1$^{−/−}$, C5ar1$^{−/−}$, and C3ar1$^{−/−}$ C5ar1$^{−/−}$ mice were isolated (three to five animals per group), total cell numbers were counted, and the CD3$^{+}$ fraction was determined by flow cytometry (WT=10%, C5ar1$^{−/−}$=5.4%, C3ar1$^{−/−}$=6.3, and C5ar1$^{−/−}$ C3ar1$^{−/−}$=4.1%). (F) Immediately after isolation and labeling, 10$^{6}$ CFSE-labeled WT T cells and CellTracker Red CMTPX-labeled C5ar1$^{−/−}$ C3ar1$^{−/−}$ T cells were adoptively cotransferred into the same SCID mice (n=4 mice per group for each time point). Surviving cells numbers were assayed at increasing times. Repeated experiments switching the dyes gave the same results (data not shown). All experiments were performed at least twice with comparable results. *p<0.05 WT versus C5ar1$^{-/-}$ C3ar1$^{-/-}$ cells. All error bars are ±SD.

The In Vivo Half-Lives of Naive T Cells are Shorter in the Absence of C5aR+C3aR Signaling To document that the relationship between C5a-C5aR+ C3a-C3aR interactions and viability is relevant physiologically, we compared the number of $CD3^+$ T cells in spleens of naive $C5ar1^{-/-}$, $C3ar1^{-/-}$, and $C5ar1^{-/-}$ $C3ar1^{-/-}$ mice to those in spleens of WT mice. The cell counts revealed 2-, 2-, and 3-fold fewer $C5ar1^{-/-}$, $C3ar1^{-/-}$, and $C5ar1^{-/-}$ $C3ar1^{-/-}$ T cells, respectively, than WT $CD3^+$ T cells per spleen (FIG. 7E). Because total cell number at steady state is a reflection of production and destruction, we performed the more direct test of in vivo cell survival. We coadoptively transferred equal numbers of naive CellTracker Red CMTPX-labeled $C5ar1^{-/-}$ $C3ar1^{-/-}$ and CFSE-labeled WT T cells together into SCID mice and determined the number of viable cells in spleens after the transfer (FIG. 7F). Similar numbers of each T cell population were detectable 8-24 hr, indicating that the cells equally migrated to spleens after the injection. However, significantly fewer $C5ar1^{-/-}$ $C3ar1^{-/-}$ T cells were detectable in the recipient spleens on days 2-5, consistent with the conclusion that viability is reduced. Control studies in which the cell-membrane labels were switched yielded the same results (data not shown). These studies thus documents that tonic C5a-C5aR and C3a-C3aR signal transduction functions in vivo to maintain the viability of naive T cells.

Experimental Procedures

Reagents and Antibodies

Murine C5a was from Cell Sciences (Canton, Me.). Mouse C3a and C5a mAbs were from R&D Systems (Minneapolis, Minn.). Anti-CD40L mAb was from Bio Express (West Lebanon, N.H.). Anti-C5aR and anti-C3aR were purchased from Santa Cruz Biotech (Santa Cruz, Calif.). The PI-3K inhibitors were provided by Dr. Kevin Shokat.

Animals $C3^{-/-}$, C5-deficient, and $CD40^{-/-}$ mice were from Jackson labs (Bar Harbor, Me.). $C3^{-/-}$ mice and $C3ar1^{-/-}$ and $C5ar1^{-/-}$ were gifts of Dr. Michael Carroll and Dr. Craig Gerard (Harvard Medical School and Children's Hospital, Boston, Mass.). Marilyn (MAR) transgenic was a gift of Polly Matzinger, Ghost Lab, NIH. We generated $Hc^{-/-}$ $C3^{-/-}$ mice by crossing C5-deficient B10.2 mice with C57BL/6 congenic $C3^{-/-}$ mice. $C5^{+/+}$ $C3^{+/+}$ littermates used as controls displayed comparable results to the studies with C57BL/6 mice as controls.

RNA Purification, cDNA Synthesis, and qPCR

Cells were purified for 5 min at 20° C. with Trizol (Invitrogen, Carlsbad, Calif.) according to the manufacturer's instructions. When C3aR and C5aR mRNAs were analyzed, preparations were treated with DNase I (standard protocol) for removal of genomic DNA. We synthesized cDNAs by incubating 20 µl of mRNAs in Sprint PowerScript Single Shots (Clontech, Mountain View, Calif.). A total of 10 µl of diluted cDNA were mixed with 2 µl of primer and 10 µl SYBR green master mix (Applied Biosystems, Foster City, Calif.) and assayed in triplicate on an ABI prism 7000 cycler. In all assays, fold increases are relative to each basal level and standardized to Actin.

Murine DCs and T Cells

Bone-marrow cells were grown in RPMI 1640/10% FBS containing 10 µg/ml IL-4+10 µg/ml GM-CSF. Fresh media with the same cytokines was added on day 3, 10 µg/ml IL-4 and 5 µg/ml GM-CSF were added on day 5, and cells were used on day 6. T cells harvested from spleens were purified with T cell enrichment columns (R&D Systems).

Anti-CD3 and Anti-CD28 Stimulations

Cells were stimulated for 1 hr with 1 µg/ml anti-CD3 and/or anti-CD28 (BD Biosciences) in serum-free RPMI 1640 for qPCR analyses and for 72 hr for IFNγ ELISPOT assays.

Immunoprecipitations

Cells were washed twice with PBS and extracted on ice for 10 min with 1% NP-40, 150 mM NaCl, 1 mM PMSF, 0.4 mM EDTA, and a protease-inhibitor cocktail (Complete Mini, Roche, Mannheim, Germany). After centrifugation of extracts for 10 min at 13,000×g, supernatants were incubated for 1 hr at 4° C. with appropriate antibody, after which Sepharose A beads were added and the mixture incubated overnight at 4° C. Centrifuged pellets were washed 5×, SDS sample buffer was added, and boiled samples were loaded onto SDS-PAGE gels.

Immunoblotting

All blots were performed by standard procedure as described (Lin et al., 2001) with HRP-conjugated secondary antibody and an ECL enhancer (GE Healthcare, Buckinghamshire, UK).

Quantitation of Murine C3 mRNA

A cDNA library was made from a C57BL/6 liver. The C3 standard was amplified with the qPCR primer for C3 via conventional PCR and diluted to $10^6$ copies/µL. A standard curve was created with 10-fold dilutions of the C3 standard and assayed by qPCR as above alongside with the cDNA libraries from total RNA isolated from the T cells and DCs. A standard curve was constructed from the CT values of the C3 standard, and the copies/µL of the samples were determined. We used the amount of total RNA from each sample to determine the amount of copies/cell.

Luminex Assay

Cells were stimulated for increasing times with 1 µg/ml anti-CD3+anti-CD28 mAbs. After stimulation, cells were assayed for pAKT and tAKT with Upstate's Beadlyte assay according to the manufacturer's instructions (Upstate, NY). In brief, cells were placed on ice immediately after incubation, centrifuged at 4° C., lysed in the buffer provided by the company, incubated with the capture beads and then the detection beads, washed, and assayed on the Bioplex 2200 (Biorad, Hercules, Calif.).

Luciferase Activity Assay

The base pairs +72 to −991 of the human B7.1 promoter were inserted into a luciferase reporter vector (GL4) then transfected into THP-1 cells by electroporation ($6 \times 10^6$ cells in 200 µl OptiMEM at 250 V and 950 µF). Cells were incubated overnight in RPMI 1640 and 10% FBS, after incubation at 37° C. for 2 hr with 300 nM C5a in serum-free RPMI 1640; luciferase activity was measured with a Lmax Luminometer (Molecular Devices).

In Vitro Cell Viability

Mouse T cells purified by EasySep magnetic bead cocktails (StemCell Technologies, British Columbia) were cultured in 96-well plates in serum-free HL-1 media containing L-glutamine and penicillin+streptomycin for the indicated times or were cultured in complete RPMI 1640 (5% FBS, L-glutamine, penn/strep). In some experiments, live and dead cells were counted with trypan blue (Invitrogen, Carlsbad, Calif.). In others, cells were stained with Cy5-anti-CD4/CD8, FITC-anti-CD44, and propidium iodide, mixed with Flow-Check Fluorspreres (Beckman Coulter, Miami, Fla.), and analyzed on a LSR II flow cytometer. Samples were normalized to 1000 Flow Check bead events.

In Vivo Cell Viability $CD4^+$ T cells from WT mice were labeled with CFSE (Invitrogen), and $C5ar1^{-/-}$ $C3ar1^{-/-}$ mice were labeled Cell-Tracker Red CMTPX (Invitrogen); afterward, $2 \times 10^6$ of each type was injected via tail vein into SCID mice. At various time points, two mice from each group were sacrificed, and total spleen cells were assayed for percentage of labeled cells by flow cytometry.

EXAMPLE 2

C5a Enhances Cell Survival in 3 Cancer Cells Lines

FIG. 2 shows that C5a enhances cell survival in three kinds of cancer cell lines in comparison with control during 72 hr culture. (a) MCA 205, (b) B16/F10 and (c) E0771. Data are representative of two experiments with duplicates. MCA 205 and E0771 were treated with 500 nM C5a and B16/F10 was treated with 100 nM C5a respectively.

Experiment Procedure

Three kinds of cancer cell lines (B 16/F10, MCA 205 and E0771) were used for this experiment. Each cell line was cultured in 12-well plates ($3 \times 10^4$/well) in serum reduced Opti-MEM media (Invitrogen) containing L-glutamine and penicillin+streptomycin for the indicated times (24 hr, 48 hr and 72 hr). C5a (Cell Sciences) in PBS was added in each well at 0, 24 and 48 hr time point to a final concentration 100 nM for B16/F10 and 500 nM for MCA205 and E0771 based on the preliminary experiment. At each time point (24 hr, 48 hr and 72 hr), live cells were trypsinized and counted using trypan blue (Invitrogen, Carlsbad, Calif.). Experiment was repeated two times with duplicates.

EXAMPLE 3

Disabling C5aR/C3aR Signal Transduction in Neoplastic Cells Induces their Apoptosis#

As shown in Example 1, naïve T cells and antigen presenting cells (APCs) partners locally synthesize C5, locally generate C5a/C3a anaphylatoxins, and upregulate surface expression levels of C5a/C3a receptors (C5aR/C3aR), both of which are G coupled protein receptors (GPCRs). Studies in which we disabled GPCR signal transduction resulting from interactions of the locally produced C5a/C3a with upregulated C5aR/C3aR on the two partners showed that this GPCR transduction is essential for AKT phosphorylation in T cells which confers both costimulatory and survival signals to T cells. Other work by our group on T cell allo-responses that occur in transplantation showed that the absence of the GPCR signaling initiates programmed cell death (PCD) via a Fas and Bcl-2-dependent mechanisms. Moreover, other work directed at understanding how T cell responses are terminated showed that its absence also initiates PCD via Bcl-2/Bcl-xl downregulation and reciprocal Bax/Bim upregulation.

Based on a possible parallel between the mechanism underlying survival/expansion/PCD in the immune system and in cancer, we investigated whether C5a/C3a.C5aR/C3aR interactions occur in tumor cells and, if so, how they impact tumor cell growth. We performed both in vitro and in vivo studies using three different murine tumor cell lines i.e. melanoma, fibrosarcoma, and breast. We found that in all three cancers, C5a/C3a.C5aR/C3aR interactions occur, and that disabling the GPCR signal transduction resulting from these interactions suppresses tumor cell expansion by initiating PCD.

Tumor Cells of 3 Different Origins Express Both C5aR and C3aR, Locally Synthesize C3/fB/fD/C5, and Generate C5a and C3a.

Figure 8C:
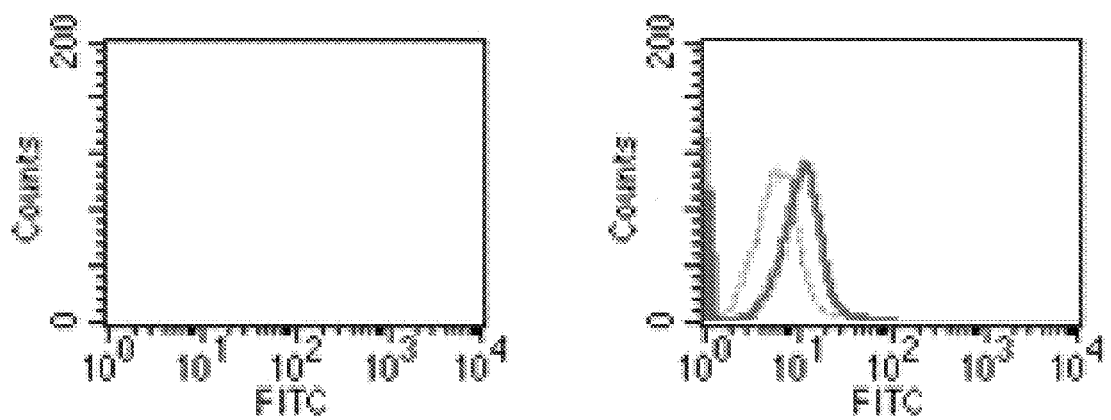
FIG. 8 illustrates C3aR and C5aR expression in 3 cancer cell lines (a) B 16 (melanoma cell), (b) MCA 205 (fibrosarcoma) and (c) E0771 (breast cancer).

Prior to initiating studies of C5a/C3a.C5aR/C3aR signaling in our 3 established tumor lines, we examined each for expression of C5aR and C3aR and for local synthesis of the several complement components involved in the generation of the C5a C3a ligands. Flow cytometric assays (FIG. 8A) showed that all three lines expressed both receptors. qPCR of RNA isolated from each line showed transcripts for C3/fB/fD/C5 Immunoblots of 4 hr.culture supernatants of each tumor line probed with anti-C5a and anti-C3a mAbs (that selectively react with C5a and C3a and not parental C5 and C3) showed both anaphylatoxins.

In vitro Abrogation of C5a/C3a-C5aR/C3aR Signaling in Tumor Cells Induces Markers of PCD.

Figure 9A:
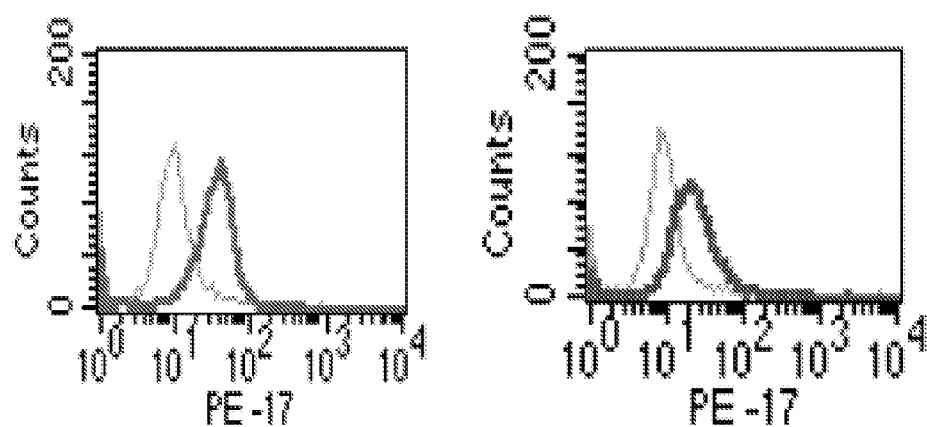
FIG. 9 illustrates Fas and FasL expression in 3 cancer cell lines. In vitro, 3 cancer cell cultures were treated with C3a/C5a receptor antagonists, trypsinized at the indicated time point after the treatment. PE labeled anti-Fas or FasL antibody was added to each sample at concentrations raging from 0.01-10 ug/ml and Fas and FasL expression were analyzed by flow cytometry: Both Fas and FasL expression were upregulated by receptor antagonists in (a) B16 within 2 hr after treatment. FasL expression in (b) MCA 205 was upregulated by 24 hr receptor antagonist treatment but Fas was not. FasL expression was slightly upregulated by 2 hr receptor antagonist treatment in (c) E0771.
Figure 9B:
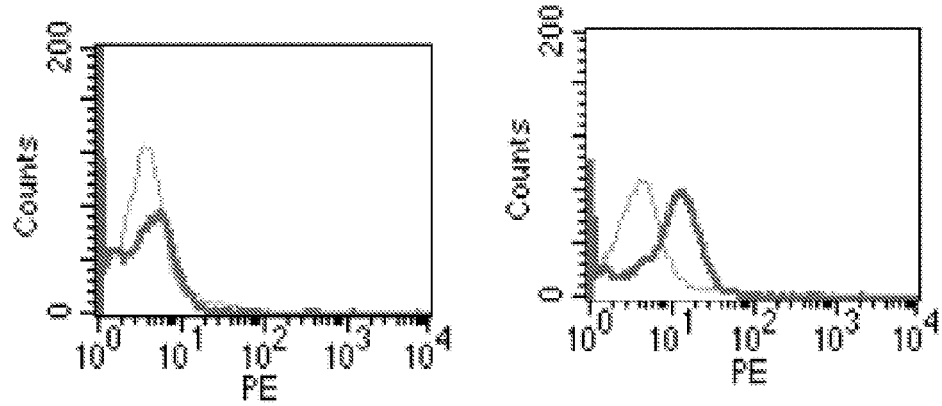
Figure 9C:
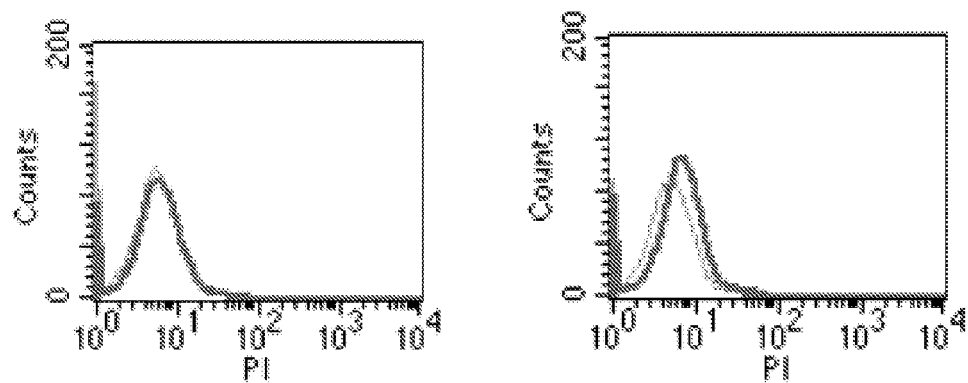
Figure 10A:
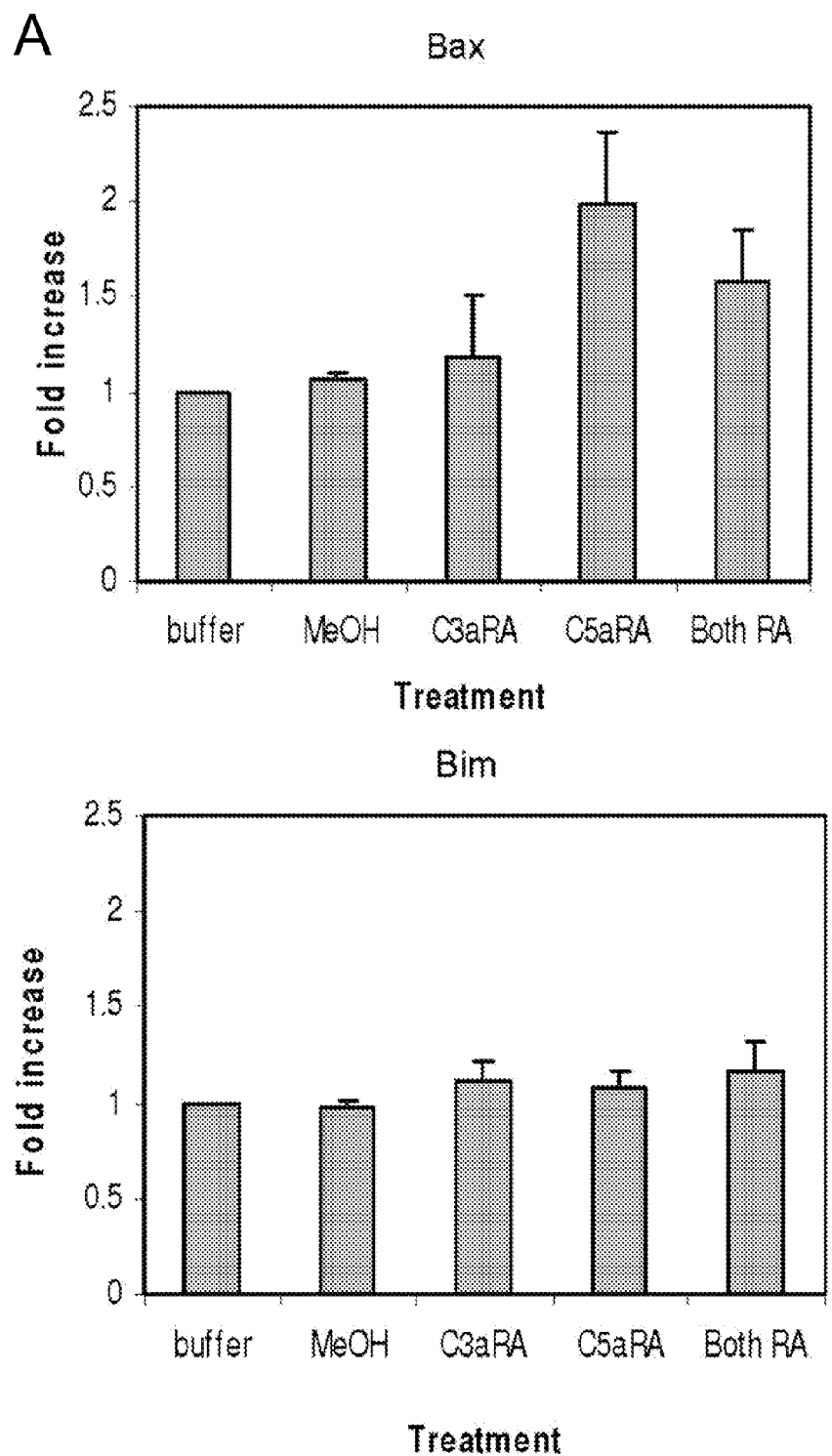
FIG. 10 illustrates qPCR assay for anti- and pro-apoptotic factors in 3 cancer cell lines: In vitro 3 cancer cell cultures were incubated for 6 hr with C3a/C5a receptor antagonist, non-treated control, MeOH and mouse IgG, and assayed for mRNA expression of anti-(Bcl-2 and Bcl-xL) and pro-(Bax and Bim) apoptotic factors by qPCR. Bcl-2, Bcl-xL, Bax and Bim in (a) B16 (b) MCA 205 and (c) E0771, respectively. Primer sequence for pro- and anti-apoptotic factors used in this experiment are mBcl-2 forward: 5'-GAC GTC TCC TCT CAG GCC CC-3' (SEQ ID NO: 1), reverse: 5'-TCA CGA CGG TAG CGA CGA GA-3'(SEQ ID NO: 2), mouse Bcl-xL forward: 5'-GGTCGCATCGTGGCCTTT-3' (SEQ ID NO: 3) and reverse: 5'-TCCGACTCACCAATACCTGCAT-3' (SEQ ID NO: 4), mouse Bim, forward: 5'-CGACAGTCTCAG-GAGGAACC-3'(SEQ ID NO: 5), reverse: 5'-CCTTCTC-CATACCAGACGGA-3' (SEQ ID NO: 6) and mouse Bax forward: 5'-CTG ACC TTG GAG CAG CCG CC-3' (SEQ ID NO: 7) and reverse: 5'-GTC CAC GTC AGC AAT CAT CC-3' (SEQ ID NO: 8). Data shown are means±standard deviations.
Figure 10B:
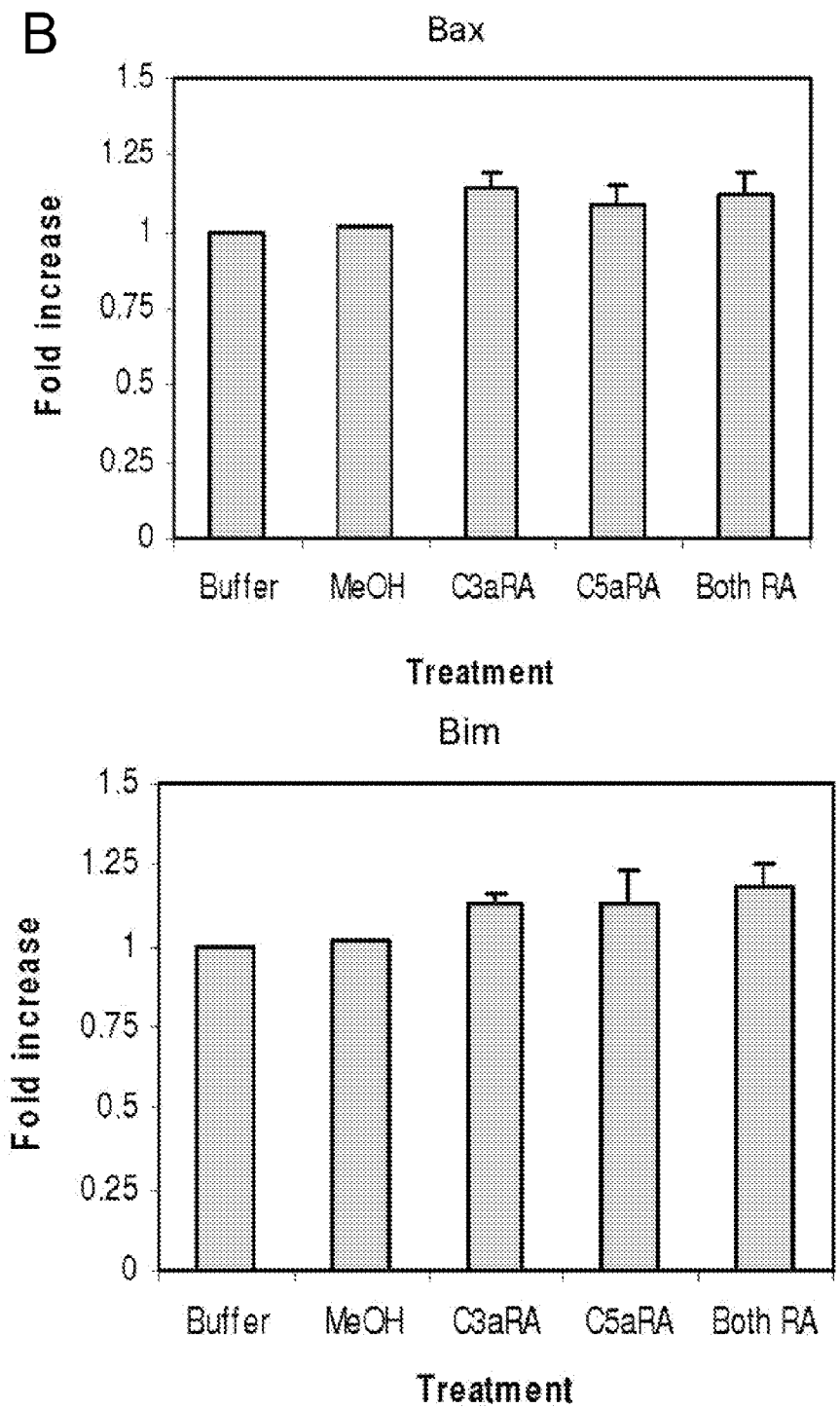
Figure 10C:
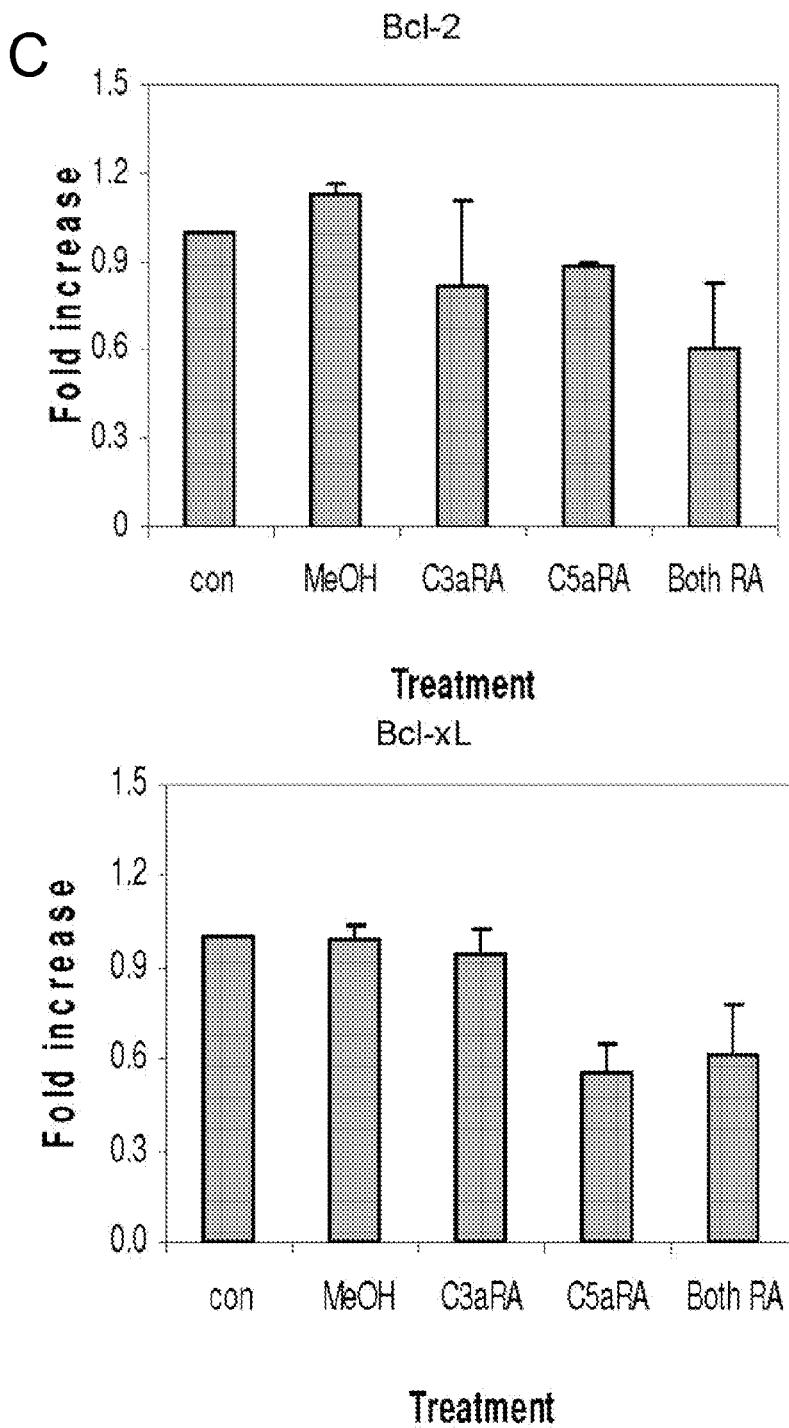

Our studies of CD4$^+$ T cell activation showed that disabling C5a/C3a.C5aR/C3aR signal transduction initiated PCD. Consequently, in the next set of experiments we cultured each of the 3 murine tumors either with 1) a mixture of the two receptor antagonists (C5aR-A+C3aR-A), or 2) a mixture of the anti-C5a+anti-C3a mAbs. At progressively increasing times after initiating the incubations, we assayed the tumor cells for surface expression of Fas and FasL by flow cytometry, and examined RNA from the cells for Bcl-2/Bcl-xl/Bax/Bim mRNA levels by qPCR. By 24 hr the inclusion of C5aR/-A/C3aR-A or anti-C5a/anti-C3a mAbs in the melanoma and breast cancer cultures (FIGS. 9 and 10) induced surface expression of Fas and FasL as well as down-regulation of Bcl-2/Bcl-xl transcripts and reciprocal up-regulation of Bax/Bim transcripts; by 48 hr the amplitude of each apoptotic change further increased. The same sequence of events occurred in the fibrosarcoma cultures but at a slower rate.

The In Vitro Induction of Apoptotic Markers Leads to Tumor Cell Death.

Figure 11A:
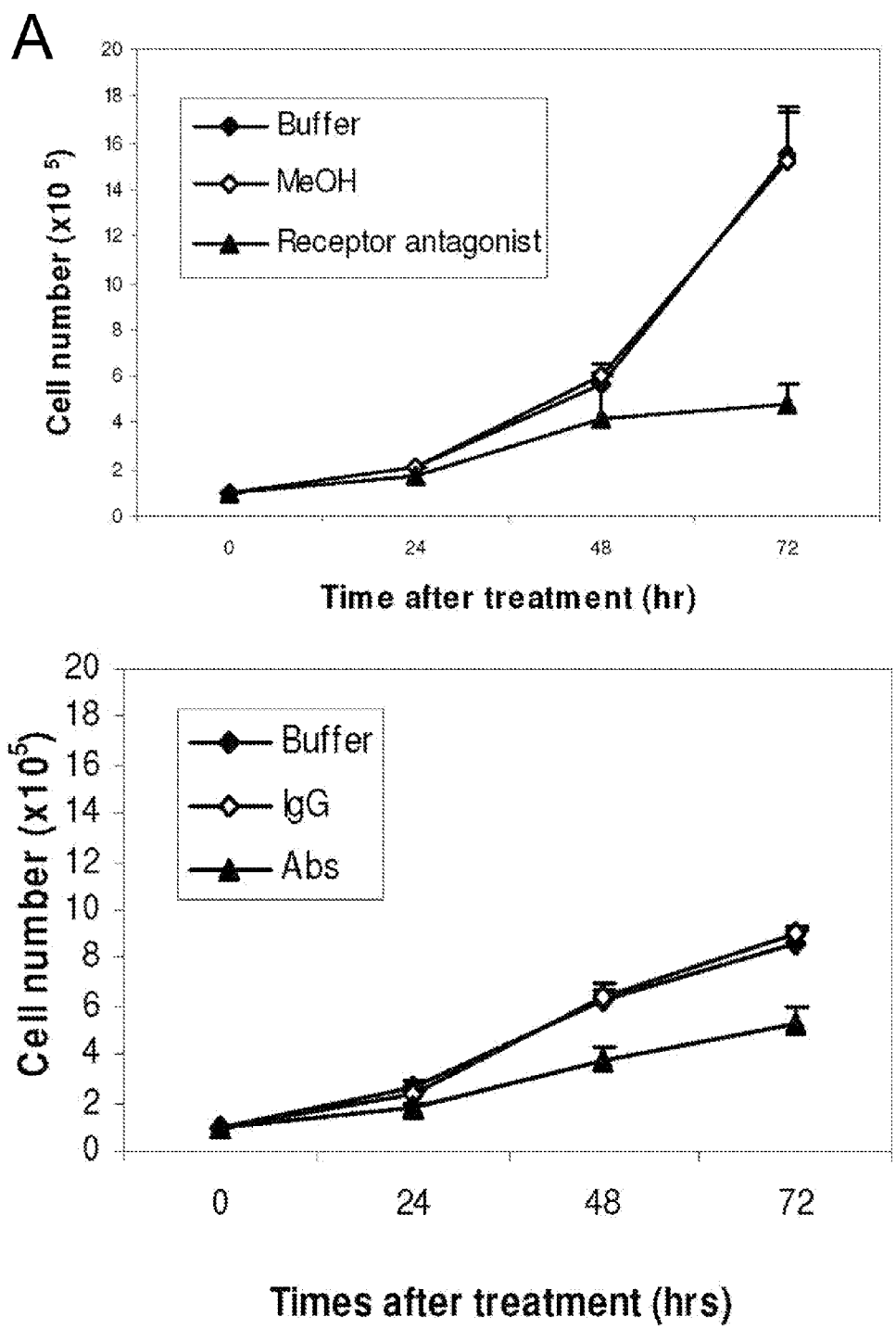
FIG. 11 illustrates, cell viability in 3 cancer cell lines incubated with receptor antagonist or α-C3a and α-C5a mABs.
Figure 11B:
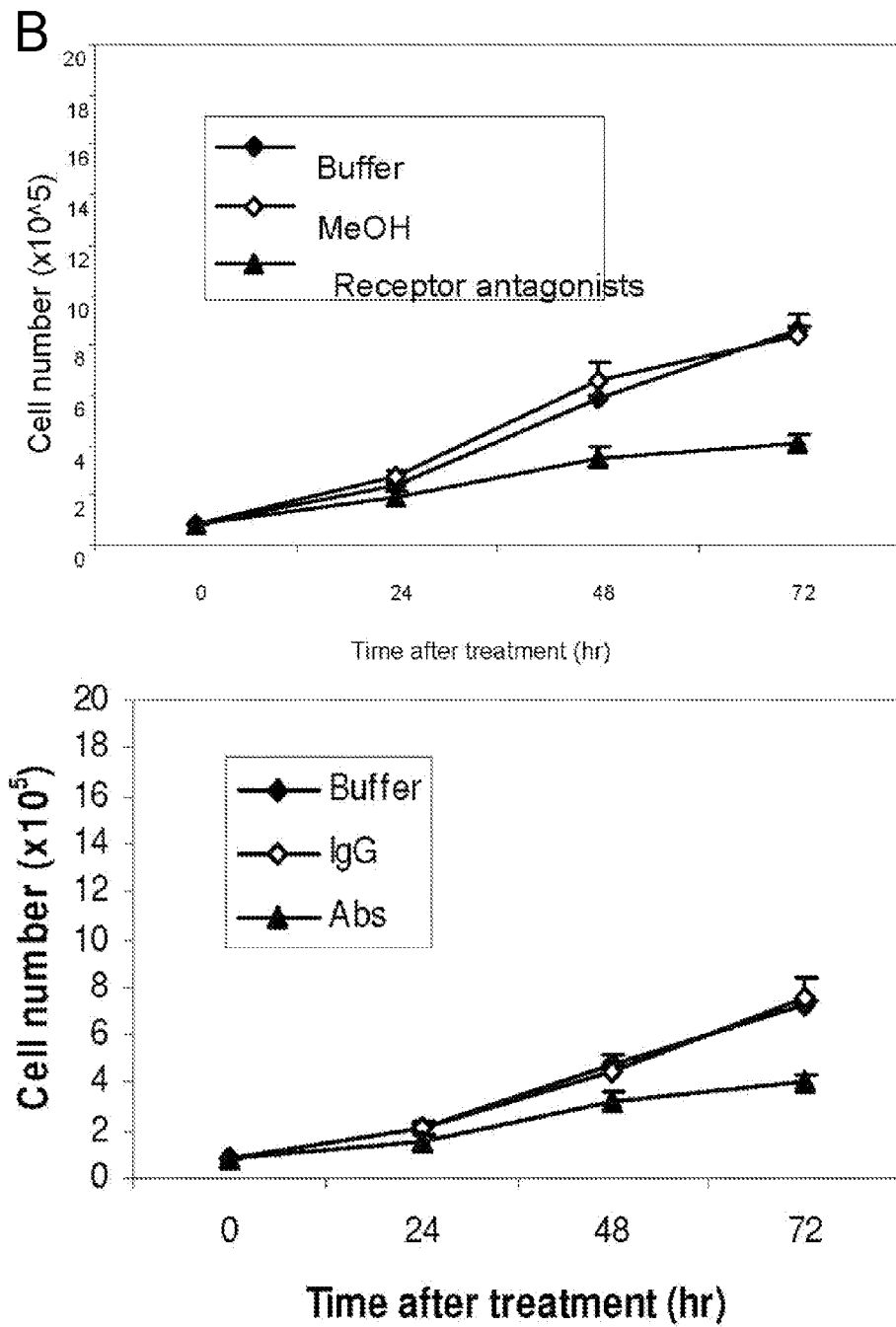
Figure 11C:
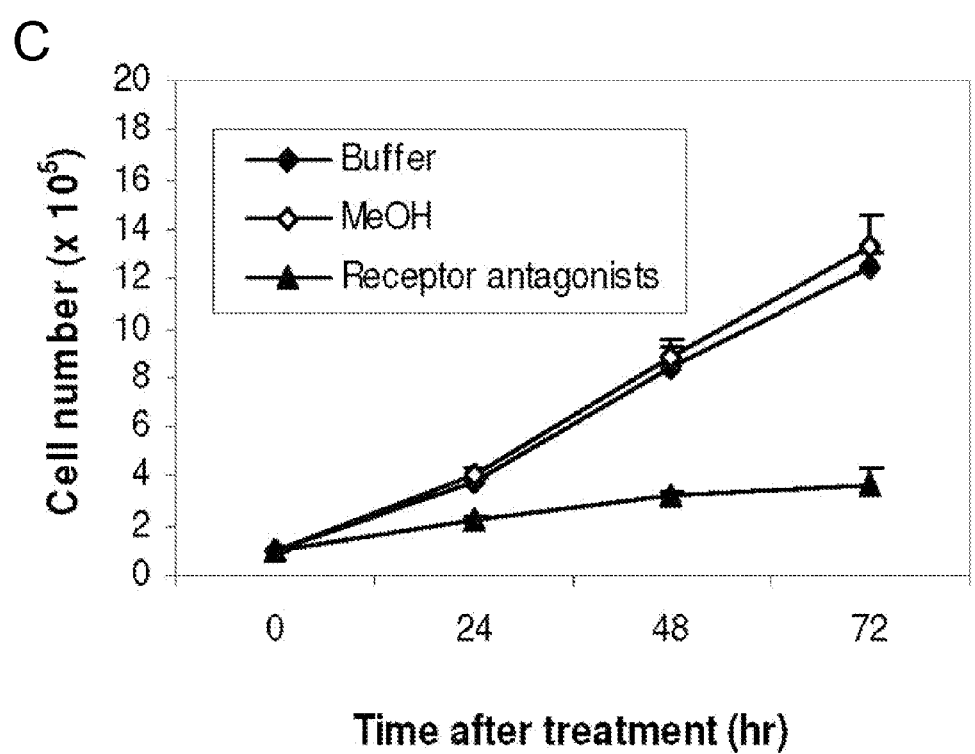

To verify that the above documented alterations associated with PCD, in fact, eventuate in tumor cell death, we next repeated the above studies, this time counting tumor cell numbers at progressively increasing times. These kinetic analyses (FIGS. 11-12) showed that compared to vehicle controls in the case of the receptor antagonists, and nonrelevant isotype controls in the case of the anti-C5a/anti-C3a mAbs, the appearance of the PCD markers and the acquisition of Annexin V positivity overlapped. To further document that the tumor cells underwent apoptosis, we performed tunnel assays which showed characteristic intracellular staining in all 3 tumors.

Figure 13C:
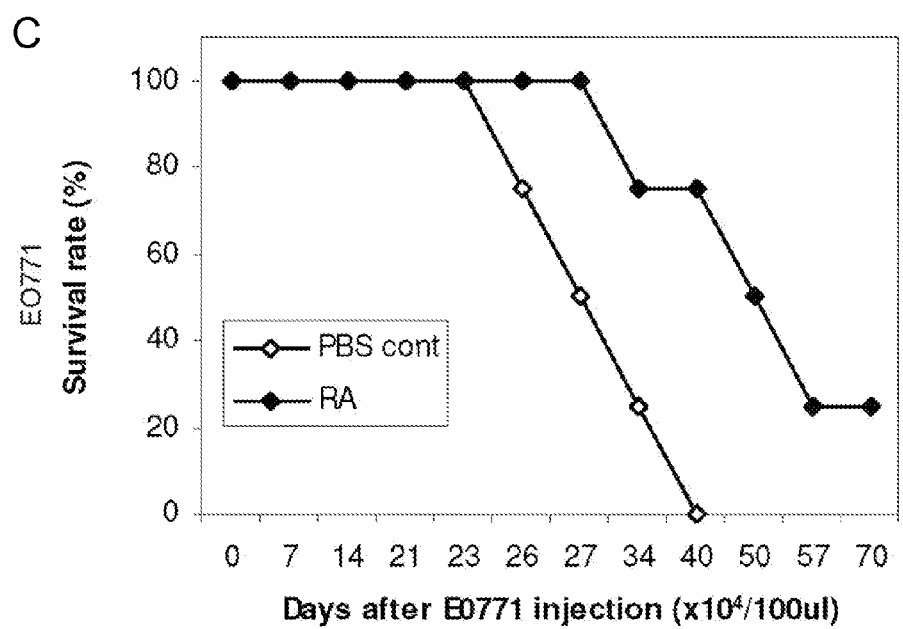
FIG. 13 illustrates in vivo experiments with SCID mice: (a) Survival rate of SCID mice challenged with cancer cell (10$^4$ cells/100 ul HBSS) followed by C3a/C5a receptor antagonist administration (1 mg/kg) was analyzed. (b) Survival rate of SCID mice challenged with cancer cell (10$^4$ cells/100 ul HBSS) followed by α-C3a and α-C5a mABs administration (1 mg/kg) was analyzed. (c) Survival rate of SCID mice challenged with cancer cell (10$^4$ cells/100 ul HBSS) followed by combination of C3a/C5a receptor antagonist and α-C3a and α-C5a mABs' administration (1 mg/kg) was analyzed.

Disabling Tumor Cell C5a/C3a.C5aR/C3aR Signal Transduction Reduces Tumor Cell Growth in vivo and Blocking Both the Receptors and the Ligands Suppresses Most Effectively Having found the interrupting tumor cell C5aR/C3aR signal transduction in vitro induces tumor cell apoptosis, we next tested whether interrupting this signal transduction can suppress tumor cell viability and growth in vivo. To eliminate any potential adaptive immune effects, we first performed studies with SCID mice. In these studies, we used the melanoma cell line and assessed the impact on tumor growth of administering 1) C5aR-A/C3aR-A, 2) anti-C5a/anti-C3a mAbs, or 3) the antagonists and the mAbs in combination. For the studies with C5aR-A/C3aR-A, we injected the antagonists or vehicle control intraperitoneally (ip) every other day. For the studies with the anti-C5a/anti-C3a mAbs, we injected the mAbs and isotype controls weekly. For the studies in which we used the antagonists together and the mAbs together, we combined the two protocols. In each treatment protocol, we inoculated the mice with $10^4$ tumor cells intravenously (iv) and used survival as the outcome measure. The first set of studies (FIG. 13A) showed that the receptor antagonists prolonged survival. The second (FIG. 13B) showed that the mAbs prolonged survival even longer. The third (FIG. 13C) showed that the combination prolonged survival markedly most efficiently.

Disabling Tumor Cell C5a/C3a.C5aR/C3aR Signal Transduction by Combining Receptor Blockade and Ligand Neutralization Efficiently Retards Tumor Cell Expansion in WT Mice Based on the above findings in SCID mice, we examined whether the same effect would apply in WT mice. We performed these studies using an identical protocol to that used with the SCID mice but this time examining all three tumor cell lines. These analyses showed combined C5aR-A/C3aR-A and anti-C3a/anti-C5a mAb treatment prolonged survival of melanoma cell recipients 2-fold, breast cancer cell recipients 3-fold, and fibrosarcoma cell recipients 4-fold. Euthanizing mice three weeks after tumor inoculation and examination of tissues histopathologically showed that the combined treatment markedly reduced both tumor mass and extent of metastases.

Interruption of Tumor Cell C5a/C3a.C5aR/C3aR Signal Transduction Abrogates EGF Induced Phosphorylation of EGF Receptor (EGFR).

Unregulated EGFR signaling has causally linked with certain cancers. Additionally, an earlier study in the literature reported that added C5a can induce EGFR phosphorylation in HeLa cells. Based on these two findings, we next asked whether EGFR phosphorylation in cancers cells is in fact dependent on C3aR/C5aR signal transduction. To do this, we cultured each of the 3 tumor lines in the presence of buffer alone, C5aR-A/C3aR-A and anti-C3a/anti-C5a mAb, or vehicle and nonrelevant mAb controls. After 2 hr, we added increasing amounts of EGF, 2 min after which we extracted the cells with NP-40 lysis buffer. We then immuoprecipitated EGFR from lysates with specific antibody and probed immunoblots of the precipitates with anti-phosphtyrosine mAb. These assays showed that the blockade of the C3aR/C5aR signal transduction abrogated EGFR phosphorylation irrespective of EGF concentration. Our studies of T cell activation showed that PI 3 kinase γ (PI-3Kγ) activation is dependent on C3aR/C5aR signal transduction. To determine this C3aR/C5aR dependent step is an intermediary for EGFR phosphorylation, we repeated the above study this time using PI-103, a specific inhibitor of this enzyme. Addition of PI-103 inhibited EGFR phosphorylation in an identical fashion, indicating that one molecular link between C3aR/C5aR signal transduction and EGFR phosphorylation is PI-3Kγ activation. In a converse study, we incubated each of the 3 tumor lines without and with added C5a and measured cell growth. In all 3 cases, the added C5a increased tumor cell numbers. Analyses of PI-3Kγ immunoprecipitates showed augmented PI-3Kγ enzyme activity and analyses of anti-EGFR immunoprecipitates showed augmented EGFR phosphorylation.

Methods

Flow Cytometry

Cells were stained for surface antigens by incubating with antibodies in PBS, 0.1% BSA and 0.01% sodium azide. All antibodies were purchased from BD PharMingen (San Diego, Calif.), stained cells analyzed on a Becton-Dickinson FACScan.

RNA Purification, cDNA Synthesis, and qPCR

Cells were purified for 5 min at 20 C using TRIzol (invitrogen, Carlsbad, Calif.) and according to the manufacturer. When mRNA was analyzed, preparations were treated with DNase I (standard protocol) to remove genomic DNA. cDNAs were synthesized by incubating 20 ul of mRNAs in Sprint Power Script Single Shots (Clontech, Mountain View, Calif.). Ten μl of diluted cDNA were mixed with 2 μl of primer and 10 ul SYBR green master mix (Applied Biosystems, Foster City, Calif.) were assayed in triplicate on an ABI prism 7000 cycler. In all assays fold increases are relative to each basal level and standardized to mouse Actin.

Immunoblot

Cells were harvested at the indicated time point after treated with IgG, MeOH, C5a-/C3a-antibodies, C5a-/C3a receptor antagonists, and buffer. Equal concentrations of cell lysates were loaded and separated by SDS PAGE using 10% Tris-HCl gels and blotted on PVDF membranes. Blots were probed with anti-mouse p-AKT antibody (Cell signaling technology) and HRP conjugated secondary antibody, and visualized with ECL (Amersham Biosciences, Piscatway, N.J., USA). Also, blots were reprobed with anti-mouse toal AKT antibody (Cell signaling technology) as an internal standard.

Cell Viability

Cells were cultured in 6-well plates in complete RPMI 1640 or DMEM media containing 10% FBS, L-glutamine and penn/strep for the indicated times. Live and dead cells were counted using trypan blue (Invitrogen, Carlsbad, Calif.) at each time point.

Annexin V Assay

Cells counted and plated in a 6-well plate as $0.5 \times 10^6$ cells/well were treated with receptor antagonists or α-C3a and α-C5a mABs. Cells collected at the indicated time point were stained either PI or annexinV-FITC alone or both and incubated for 10 min at room temperature in the darkness. Further process was followed by manufacturer's manual (BD Pharmingen).

Animals and In Vivo Experiments

To investigate whether C3a/C5a receptor antagonist functions to induce apoptosis of cancer cells in vivo, Scid (severe combined immuno deficiencent) mice and C57BL/6 mice were purchased from Jackson labs (Bar Harbor, Me.). Each mouse was challenged with $2 \times 10^4$ cells/100 ul HBSS (Hank's balanced salt solution) by i.p. injection. For the treatment group, receptor antagonists solution (100 uM in HBSS) was injected by i.p. injection into each mouse every second day until the experiment terminated. For the control group, the same amount of HBSS was injected into each mouse in the same way.

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, we claim:

1. A method of inducing apoptosis in a cancer cell expressing a C3a receptor (C3aR) and a C5a receptor (C5aR), the method comprising: administering amounts of a C3aR antagonist and a C5aR antagonist directly or locally to the cancer cell; wherein the amounts of the C3aR antagonist and the C5aR antagonist administered to the cancer cell are effective to substantially reduce or substantially inhibit the activity of protein kinase B (PKB) in the cancer cell and induce apoptosis in the cancer cell, and wherein the C3aR antagonist inhibits C3a mediated C3aR signaling of the cancer cell and the C5aR antagonist inhibits C5a mediated C5aR signaling of the cancer cell.

2. The method of claim 1, the C3aR antagonist and the C5aR antagonist being selected from the group consisting of a small molecule, a polypeptide, and a polynucleotide.

3. The method of claim 2, the C3aR antagonist being an antibody directed against C3aR and the C5aR antagonist being an antibody directed against C5aR.

4. The method of claim 2, the polynucleotide comprising a small interfering RNA directed against a polynucleotide encoding at least one of C3, C5, C3aR, or C5aR.

5. The method of claim 1, the step of administering C3aR antagonist and the C5aR antagonist includes administering to the cell an antibody directed against C5a and an antibody directed against C3a.

6. A method of treating cancer in a subject, the method comprising: administering directly or locally to cancer cells expressing C3aR and C5aR of a subject therapeutically effective amounts of a C3aR antagonist and a C5aR antagonist, wherein the amounts of C3aR antagonist and C5aR antagonist administered to the cancer cells substantially reduce or substantially inhibit the activity of protein kinase B (PKB) in the cancer cells and induce apoptosis in the cancer cells, and wherein the C3aR antagonist inhibits C3a mediated C3aR signaling of the cancer cell and the C5aR antagonist inhibits C5a mediated C5aR signaling of the cancer cell.

7. The method of claim 6, the C3aR antagonist and the C5aR antagonist being selected from the group consisting of a small molecule, a polypeptide, and a polynucleotide.

8. The method of claim 7, the C3aR antagonist being an antibody directed against C3aR and the C5aR antagonist being an antibody directed against C5aR.

9. The method of claim 7, the polynucleotide comprising a small interfering RNA directed against a polynucleotide encoding at least one of C3, C5, C3aR, or C5aR.

10. The method of claim 6, the step of administering the C3aR antagonist and the C5aR antagonist includes administering to the cancer cell an antibody directed against C5a and an antibody directed against C3a.

11. The method of claim 6, the C3aR antagonist and the C5aR antagonist being administered locally to the cancer in the subject.

12. The method of claim 6, the C3aR antagonist and the C5aR antagonist each being conjugated to targeting moieties that target the cancer being treated.

13. A method of treating cancer in a subject, the method comprising: administering directly or locally to cancer cells expressing C3aR and C5aR of the subject therapeutically effective amounts of a C3aR antibody and a C5aR antibody to induce apoptosis in the cancer cells, wherein the C3aR antibody inhibits C3a mediated C3aR signaling of the cancer cell and the C5aR antibody inhibits C5a mediated C5aR signaling of the cancer cell.

14. The method of claim 13, wherein the C3aR antibody and the C5aR antibody are each conjugated to targeting moieties that target the cancer being treated.

15. The method of claim 13, wherein administration of the C3aR antibody and the C5aR antibody reduces or substantially inhibits the activity of protein kinase B (PKB), induces Fas/FasL surface expression, down regulates Bcl-2/Bcl-xl transcripts, up-regulates expression of Bax/Bim transcripts in the cancer cells.

16. The method of claim 1, the cancer cell being at least one of a melanoma cancer cell, fibrosarcoma cancer cell, breast cancer cell, or leukemia cancer cell.

17. The method of claim 6, the cancer being at least one of melanoma, fibrosarcoma, breast cancer cell, or leukemia.

18. The method of claim 13, the cancer being at least one of melanoma, fibrosarcoma, breast cancer cell, or leukemia.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: PRIMER

<400> SEQUENCE: 1
gacgtctcct ctcaggcccc                                           20

<210> SEQ ID NO 2
<211> LENGTH: 20
<212> TYPE: DNA
<213> ORGANISM: Artificial Sequence
<220> FEATURE:
<223> OTHER INFORMATION: PRIMER

<400> SEQUENCE: 2
tcacgacggt agcgacgaga                                           20

<210> SEQ ID NO 3
<211> LENGTH: 20
<212> TYPE: DNA
<213> ORGANISM: Artificial Sequence
<220> FEATURE:
```

```
<223> OTHER INFORMATION: PRIMER

<400> SEQUENCE: 3
tcacgacggt agcgacgaga                                                    20

<210> SEQ ID NO 4
<211> LENGTH: 22
<212> TYPE: DNA
<213> ORGANISM: Artificial Sequence
<220> FEATURE:
<223> OTHER INFORMATION: PRIMER

<400> SEQUENCE: 4
tccgactcac caatacctgc at                                                 22

<210> SEQ ID NO 5
<211> LENGTH: 20
<212> TYPE: DNA
<213> ORGANISM: Artificial Sequence
<220> FEATURE:
<223> OTHER INFORMATION: PRIMER

<400> SEQUENCE: 5
cgacagtctc aggaggaacc                                                    20

<210> SEQ ID NO 6
<211> LENGTH: 20
<212> TYPE: DNA
<213> ORGANISM: Artificial Sequence
<220> FEATURE:
<223> OTHER INFORMATION: PRIMER

<400> SEQUENCE: 6
ccttctccat accagacgga                                                    20

<210> SEQ ID NO 7
<211> LENGTH: 20
<212> TYPE: DNA
<213> ORGANISM: Artificial Sequence
<220> FEATURE:
<223> OTHER INFORMATION: PRIMER

<400> SEQUENCE: 7
ctgaccttgg agcagccgcc                                                    20

<210> SEQ ID NO 8
<211> LENGTH: 20
<212> TYPE: DNA
<213> ORGANISM: Artificial Sequence
<220> FEATURE:
<223> OTHER INFORMATION: PRIMER

<400> SEQUENCE: 8
gtccacgtca gcaatcatcc                                                    20
```